(12) United States Patent
Silvennoinen et al.

(10) Patent No.: US 8,841,078 B2
(45) Date of Patent: Sep. 23, 2014

(54) DUAL ACTIVITY KINASE DOMAINS AND USES THEREOF

(75) Inventors: Olli Silvennoinen, Tampere (FI); Daniela Ungureanu, Tampere (FI)

(73) Assignee: Genon Biotechnologies Oy, Tampere (FI)

( * ) Notice: Subject to any disclaimer, the term of this patent is extended or adjusted under 35 U.S.C. 154(b) by 0 days.

(21) Appl. No.: 13/578,051

(22) PCT Filed: Feb. 10, 2011

(86) PCT No.: PCT/FI2011/050128
§ 371 (c)(1),
(2), (4) Date: Aug. 9, 2012

(87) PCT Pub. No.: WO2011/098673
PCT Pub. Date: Aug. 18, 2011

(65) Prior Publication Data
US 2012/0309023 A1    Dec. 6, 2012

(30) Foreign Application Priority Data

Feb. 10, 2010  (FI) ................................. 20105133
May 21, 2010  (FI) ................................. 20105566

(51) Int. Cl.
*G01N 33/53* (2006.01)
*C12Q 1/48* (2006.01)
*C12N 9/12* (2006.01)

(52) U.S. Cl.
CPC .............. *C12Q 1/485* (2013.01); *C12N 9/1205* (2013.01); *G01N 2500/02* (2013.01)
USPC ........................................... 435/7.1; 435/7.2

(58) Field of Classification Search
None
See application file for complete search history.

(56) References Cited

U.S. PATENT DOCUMENTS 6,969,760 B2 * 11/2005 Ihle et al. ...................... 536/23.1
7,795,206 B2 *  9/2010 Wilks et al. ..................... 514/7.5
8,309,718 B2 * 11/2012 Li et al. .......................... 544/295

OTHER PUBLICATIONS

Feener et al. (Mol. Cellular Biol 2004 vol. 24, p. 4968-4978).*

* cited by examiner

*Primary Examiner* — Jacob Cheu
(74) *Attorney, Agent, or Firm* — Sughrue Mion, PLLC

(57) ABSTRACT

The present invention relates to a dual activity domain of JAK proteins, namely JH2. It is provided that the JH2 domain is a true and important target for drug development, especially for diseases caused by aberrant JAK signalling, such as myeloproliferative disorders and leukemias.

22 Claims, 12 Drawing Sheets

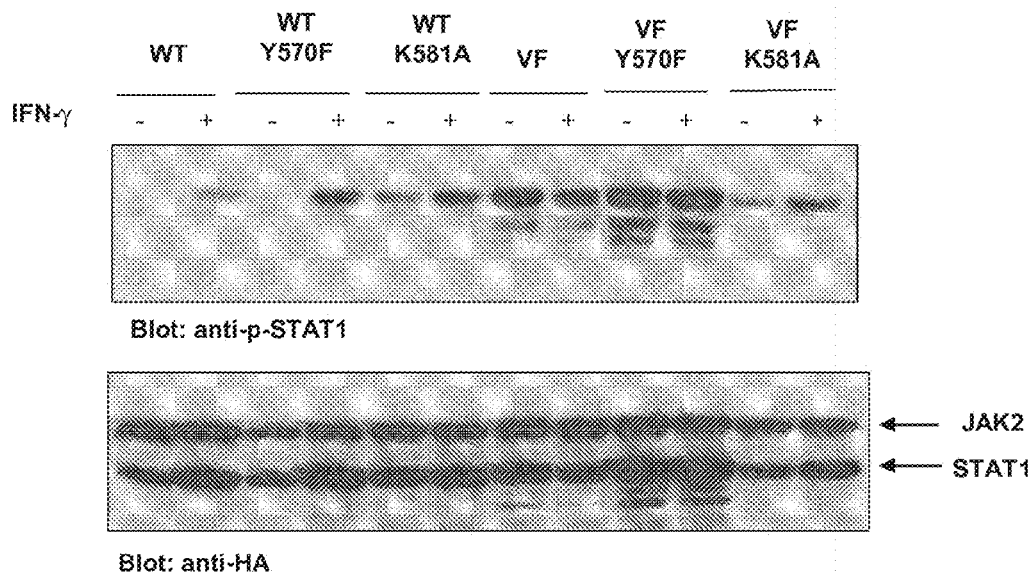
FIGURE 15
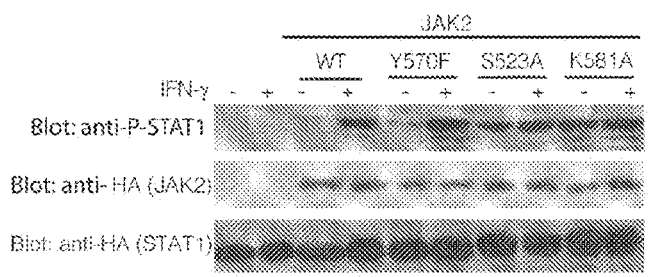
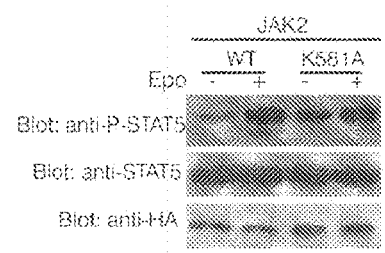
FIGURE 16A
FIGURE 16B
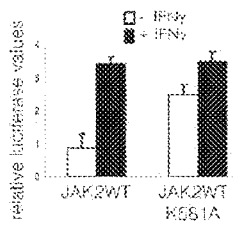
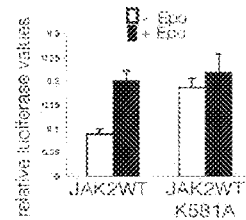
FIGURE 16C
FIGURE 16D

US 8,841,078 B2

DUAL ACTIVITY KINASE DOMAINS AND USES THEREOF

CROSS REFERENCE TO RELATED APPLICATIONS

This application is a National Stage of International Application No. PCT/FI2011/050128 filed Feb. 10, 2011, claiming priority based on Finnish Patent Application Nos. 20105133 filed Feb. 10, 2010 and 20105566 filed May 21, 2010, the contents of all of which are incorporated herein by reference in their entirety.

FIELD OF THE INVENTION

The present invention relates to assays for screening and identifying modulators of JH2 kinase activity and to applications for use in said assays.

BACKGROUND OF THE INVENTION

Janus kinases (JAKs) are non-receptor protein tyrosine kinases playing a critical role in cytokine receptor signaling in blood formation, immune responses and in several other physiological responses. The mammalian JAK protein family consists of four members, i.e. JAK1, JAK2, JAK3, and TYK2. The JAK kinases mediate the signaling of all receptors belonging to hematopoietic cytokine receptor type I and type II superfamily and they are required for the biological responses of interferons, most interleukins and colony stimulating factors, as well as hormones such as erythropoietin, thrombopoietin, growth hormone, prolactin and leptin. Due to these fundamental biological properties several cytokines such as erythropoietin, thrombopoietin, growth hormone, granulocyte- and granulocyte-macrophage colony stimulating factors, interferons, and various interleukins are used as drugs to treat human diseases such as anemia, thrombocythemia, immunological diseases, infectious diseases and certain types of cancer. On the other hand, inhibition of JAK kinases is a potent way to treat various diseases where JAK kinases are causing the disease.

The JAK proteins comprise seven different conserved domains (JAK homology domains, JH1-7) (Rane et al., Oncogene 2000, 19, 5662-5679). The carboxyl terminus contains two nearly identical domains, an active kinase domain (JH1) and a catalytically inactive pseudokinase domain (JH2) also termed as kinase-like domain (KLD). It has been generally acknowledged that JH2 lacks enzymatic activity yet it is involved in regulating the activity of JH1. Both biochemical and cell biological data as well as genetic evidence from human diseases and animal models indicate that JH2 has a dual function in regulation of cytokine signaling. JH2 is required to maintain JAK kinases inactive in the absence of cytokine stimulation, but they are also required for cytokine induced signaling. The region immediately N-terminal to the JH2 is a SH2-like domain consisting of the whole JH3 and a part of JH4. The region immediately N-terminal to the SH2-like domain is a FERM-like domain consisting of a part of JH4 and the whole JH5-JH7. Like most kinases, JAKs require autophosphorylation for their full activity. In the case of JAK2, the phosphorylation of the activation loop tyrosines 1007 and 1008 are critical for the activity.

Mutant JAKs are involved in various human pathologies including severe combined immunodeficiency (SCID) and many myeloproliferative neoplasms (MPNs) as well as different leukemias and immunological diseases. Polycythemia vera (PV) is a myeloproliferative disorder that is in most cases caused by a single point mutation in the JH2 domain (JAK2V617F) of JAK2 resulting in aberrant JAK2 signaling, erythrocyte overproduction, and a propensity for thrombosis, progression to myelofibrosis, or leading to leukaemia. The mutation constitutively activates the JAK2 tyrosine kinase and is found in majority of patients with PV and approximately 50% of patients with essential thrombocythemia (ET) and idiopathic myelofibrosis (IMF). Also other less frequent disease causing mutations in the JH2 of JAK2 have been identified in MPN patients. In addition, mutations in the JH2 domains of JAK1, JAK3 and TYK2 are linked with human diseases, particularly hematological and immunological diseases. The dual functional role of JH2 is also demonstrated in these disease associations, and gain of function mutations in JH2 cause hyperactivation of signaling and diseases related to that such as leukemias and cancer, while loss of function abrogate signaling and results in diseases like SCID. The mechanism underlying JAK activation is currently not known.

MPNs are chronic conditions that currently lack specific treatments and the management of these diseases is targeted to the alleviation of symptoms and prevention of complications associated with the conditions. For example, hydroxyurea is commonly used for reducing the number of platelets in patients with PV or ET. However, long term use of hydroxyurea is associated with an increased risk for the development of leukemia. Another commonly used agent for the management of PV and ET is anagrelide which, however, is associated with many side effects.

Increasing effort has been put on the design of MPN specific medicaments many of which are JAK inhibitors. For example, international patent publication WO 2008/057233 discloses a selective JAK2 inhibitor, TG101348, which is currently in clinical trials for the range of diseases caused by V617F-related MPNs. Further, JAK3 inhibitor CP-690,550 is on clinical trials for rheumatoid arthritis, psoriasis, transplant rejection, inflammatory bowel disease and dry eye (R Riese, S. Krishnaswami, J. Kremer (2010) Best Pract. & Res Clin Rheumatol., 24, 513). Other therapeutically potential JAK inhibitors have been disclosed e.g. in US 2009/318405, US 2007/135461, and US 2007/149506. All these inhibitors target the JH1 domain, and they are not able to discriminate between normal and mutated JAK kinase. Given the severity of MPNs and lack of clinically approved specific treatments, there is a great need for the design of further MPN and other cytokine signaling specific medicaments.

BRIEF DESCRIPTION OF THE INVENTION

The present invention describes catalytically active JH2 domains of JAK proteins, and various aspects of drug development having JH2 domain as a target.

An object of the present invention is to provide use of a JH2 domain of a JAK protein or polypeptide for screening and identifying modulators of JH2 kinase activity. Said JAK protein or polypeptide may be elected from a group consisting of JAK1, JAK2, JAK3 and TYK2. Said JH2 domain may be catalytically active or inactive depending on the details and/or purpose of the screening or the type of the modulator.

Another object of the present invention is to provide an assay for screening and identifying modulators of JH2 kinase activity. Said assay comprises the steps of a) reacting a test substance with a reaction mixture comprising a JH2 domain, ATP or an analog thereof, and divalent cations, b) determining in said reaction mixture at least one feature selected from a group consisting of JH2 autophosphorylation, substrate phosphorylation, binding of ATP or an analog thereof to the JH2 domain, binding of the test substance to the JH2 domain, binding of the substrate to the JH2 domain, ADP production, and a conformational or structural state of JH2, and c) identifying said test substance as a modulator of JH2 kinase activity if the feature determined in step b) is different from the corresponding feature determined in the absence of said test substance. In some embodiments, said test substance is identified as a modulator of JH2 activity if the said compound can compete binding of ATP/ATP analog, affect binding of JH2 to its substrate or affect the production of ADP as a product of a catalytic reaction. In some specific embodiments, said substance binding is determined by methods known to a person skilled in the art such as measuring a calorimetric change in the enthalpy and melting temperature of the JH2 domain, or change in surface plasmon resonance, spectrocopical methods including fluorescence, UV/visible light, CD, NMR based methods or microscopical methods including atom force microscopy. In some further embodiments, particularly in screening for allosteric modulators, the JH2 domain does not have to possess catalytic activity.

In some embodiments, the present assay is based on autophosphorylation of tyrosine and/or serine residues of JH2, while in other embodiments the assay is based on the ability of JH2 to catalyze transphosphorylation of a tyrosine and/or serine kinase substrate. In further embodiments, the assay is a cell based assay.

Still another object of the present invention is to provide an assay for screening and identifying modulators of JH2 kinase activity, comprising: a) expressing a JAK peptide comprising a catalytically active form of a JH2 domain in vivo in a prokaryotic or non-human eukaryotic organism, b) administering a test substance to said organism, c) determining a physiological readout, and d) identifying said test substance as modulator of JAK kinase activity if the physiological readout in step c) is different from the physiological readout in the absence of said test substance. For example, said readout may be selected from a group consisting of development of an immunological disease or immune response, a hematopoietic disease or lineage, tumor, a disease of central or peripheral neural system, a metabolic or cardiac disease, and a physiological response including growth, development, reproduction and lactation.

A further object of the present invention is to provide a kit for use in the present assays. The kit comprises a) a catalytically active form of a JAK JH2 domain alone or in combination with other JAK domains, b) at least one antibody selected from a group consisting of phosphotyrosine and phosphoserine specific antibodies, and c) means for detecting binding of said antibody to a phosphorylated residue, if any. Alternatively the kit comprises, in addition to said catalytically active JH2 domain, one or more reagents for detecting the presence of a product of a kinase reaction such as ADP. The kit may further comprise a substrate for tyrosine and/or serine phosphorylation, and reagents to detect them and detect product of kinase reaction such as ADP.

A still further object of the present invention is to provide a catalytically active JH2 domain of a JAK protein. In some embodiments, said catalytically active JH2 domain comprises an amino acid sequence selected from a group consisting of amino acid an amino acid sequence selected from a group consisting of amino acids 553-856, 567-856 or 574-856 of SEQ ID NO. 1; amino acids 513-827 or 523-827 of SEQ ID NO. 2; amino acids 512-800 or 521-777 of SEQ ID NO. 3; and amino acids 564-876, 577-876, or 571-876 of SEQ ID NO. 4.

Even still further objects of the present invention are to provide Ser523 and Tyr570 residues of JAK2 as biomarkers for a MPN disease or its progression or a therapeutic response. In some embodiments, decreased phosphorylation of JH2 serine residues such as Ser523 or tyrosine residues such as Tyr570 may serve as a biomarker for MPN disease or its progression. In some other embodiments, increased level of phosphorylation of such residues may in turn serve as a marker for a therapeutic response.

Specific embodiments of the invention are set forth in the dependent claims.

Other objects, embodiments, details and advantages of the present invention will become apparent from the following drawings, detailed description and examples.

BRIEF DESCRIPTION OF THE DRAWINGS

In the following the invention will be described in greater detail by means of preferred embodiments with reference to the attached figures, in which.

HA-tagged full length JAK2 (JAK2WT, JAK2WTY570F, JAK2WTK581A, JAK2WTK882D) proteins from transfected γ2A cells were immunoprecipitated with an anti-HA antibody and Western blotted with anti-pTyr (4G10), anti-pTyr570, or anti-pSer523, antibodies. Immunoblotting with anti-HA antibody was used for determining the protein levels after stripping.

Figure 13:
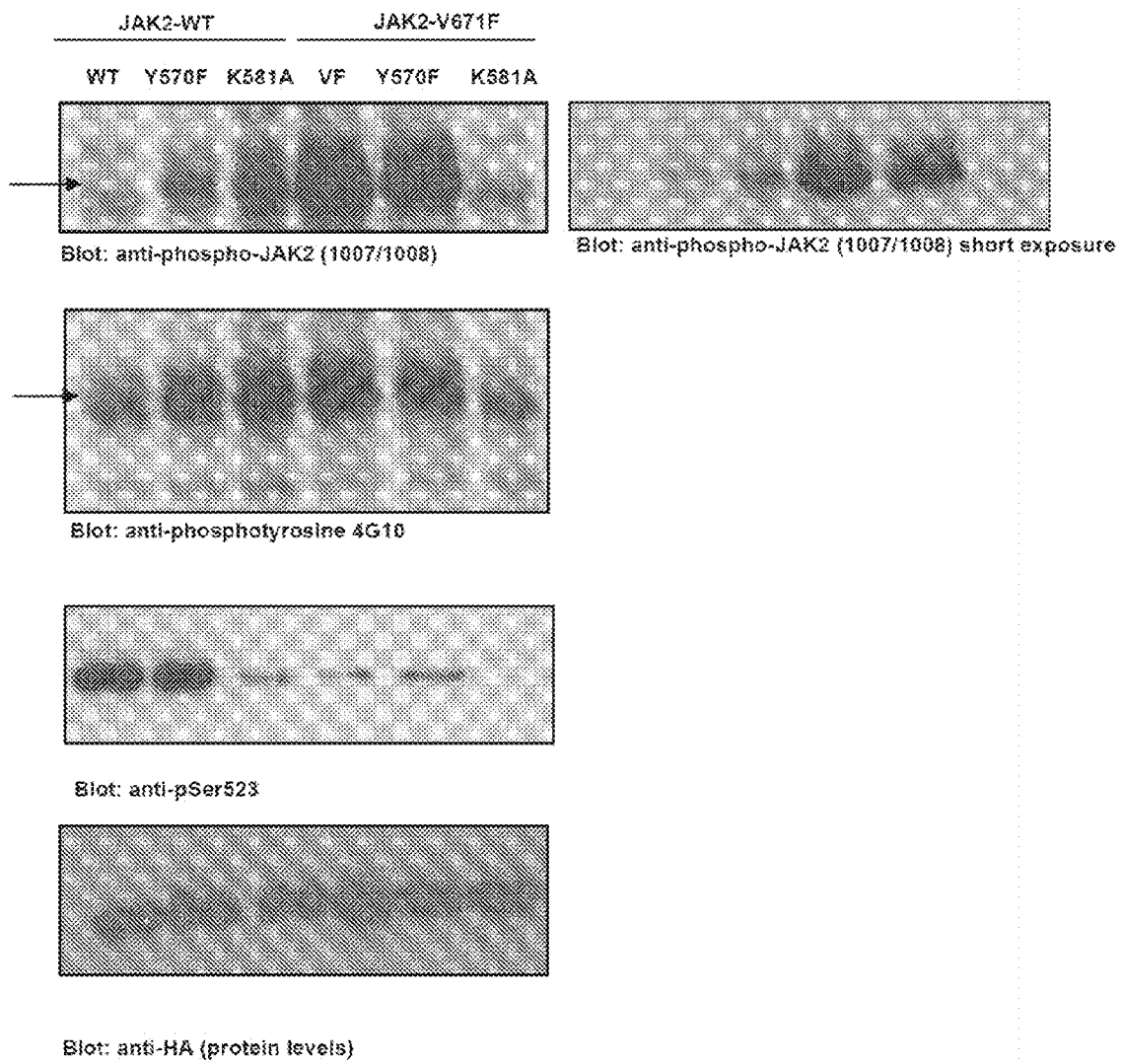

FIG. 13 is an immunoblot demonstrating that catalytic inactivation of JH2 by a K581A mutation prevents aberrant JAK activation caused by a V617F mutation. In wild type JAK2 introduction of K581A mutation abolishes Ser523 phosphorylation in cells. HA-tagged full length wild type or V617F mutant JAK2 (JAK2WT, JAK2WTY570F, JAK2WTK581A, JAK2VF, JAK2VFY570F, JAK2VFK581A) proteins from transfected γ2A cells were immunoprecipitated with an anti-HA antibody and Western blotted with anti-phospho-JAK2 (1007/1008), anti-pTyr (4G10), or anti-pSer523 antibodies. Immunoblotting with anti-HA antibody was used for determining the protein levels after stripping.

Figure 14:
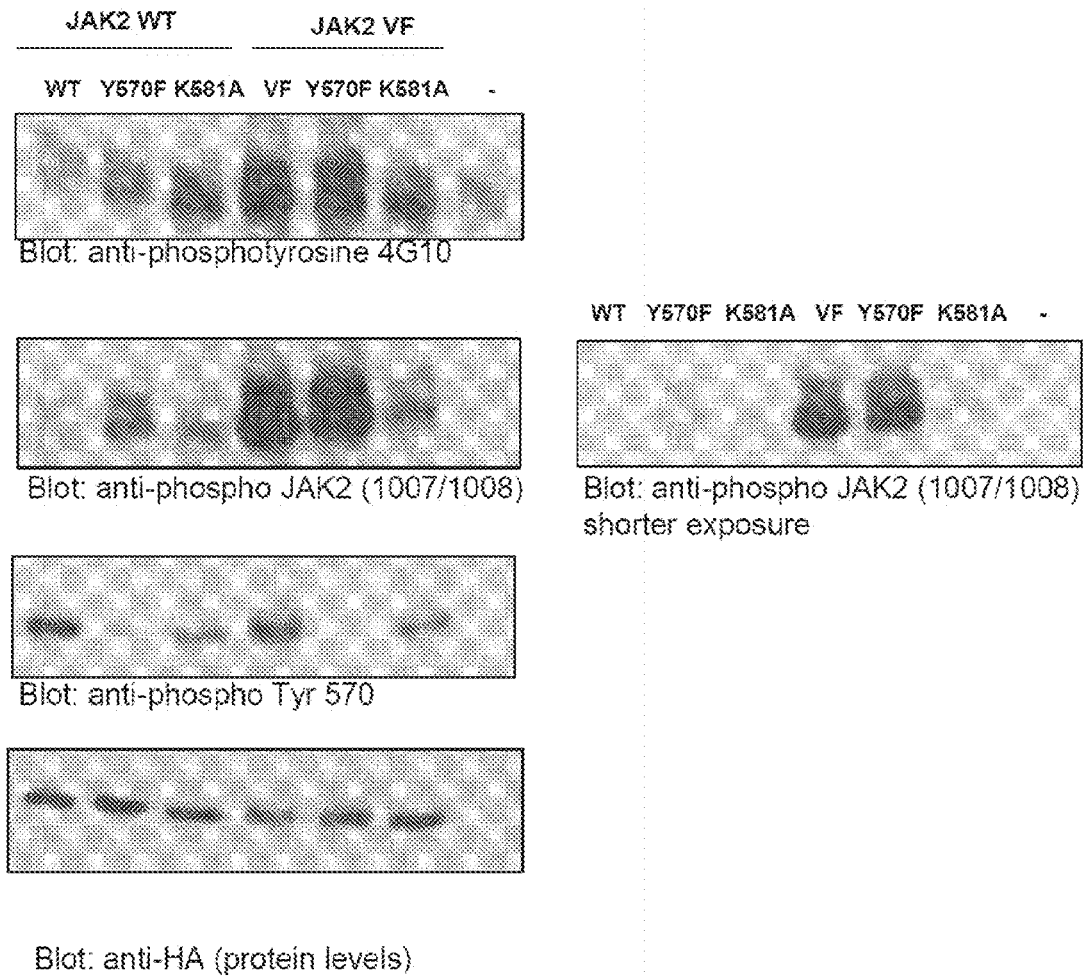

FIG. 14 is an immunoblot demonstrating that catalytic inactivation of JH2 by a K581A mutation prevents aberrant JAK activation caused by a V617F mutation, as well as inhibits Tyr570 phosphorylation in cells. HA-tagged full length wild type or V617F mutant JAK2 and mutants thereof (JAK2WT, JAK2WTY570F, JAK2WTK581A, JAK2VF, JAK2VFY570F, JAK2VFK581A) proteins from transfected γ2A cells were immunoprecipitated with an anti-HA antibody and blotted with anti-pTyr (4G10), anti-phospho-JAK2 (1007/1008), or anti-pTyr570 antibodies. Immunoblotting with anti-HA antibody was used for determining the protein levels after stripping.

FIG. 15 is an immunoblot demonstrating tyrosine phosphorylation (activation) of STAT1 by JAK2 mutants. HA-tagged full length wild type or V617F mutant JAK2 constructs (JAK2WT, JAK2VF, JAK2K581A, JAK2VFK581A) together with STAT1 expression construct were expressed in γ2A cells, the cells were starved and stimulated with cytokine (IFN-gamma) and the lysates were immunoprecipitated with an anti-HA antibody and Western blotted with anti-pSTAT1.

FIG. 16A shows an immunoblot demonstrating tyrosine phosphorylation of STAT1 in response to IFN-γ stimulation, whereas FIG. 16B shows an immunoblot demonstrating that of STAT5 in response to Epo stimulation. HA-tagged full length wild type (JAK2WT), and JAK2 Y570F and JAK2K581A mutants together with STAT1 or STAT5 construct, respectively, were expressed in γ2A cells and stimulation with hIFN-γ or hEpo. STAT phosphorylation was analysed by Western Blotting with anti-pSTAT1 antibody or anti-pSTAT5 antibody.

FIG. 16C shows the effect of JAK2 K581A mutation on STAT1-mediated transcriptional activation using IFN-γ-dependent GAS luciferase reporter, whereas FIG. 16D shows the effect of JAK2 K581A mutation on STAT5-mediated transcriptional activation using SPI-Luc2 luciferase reporter.

Figure 17:
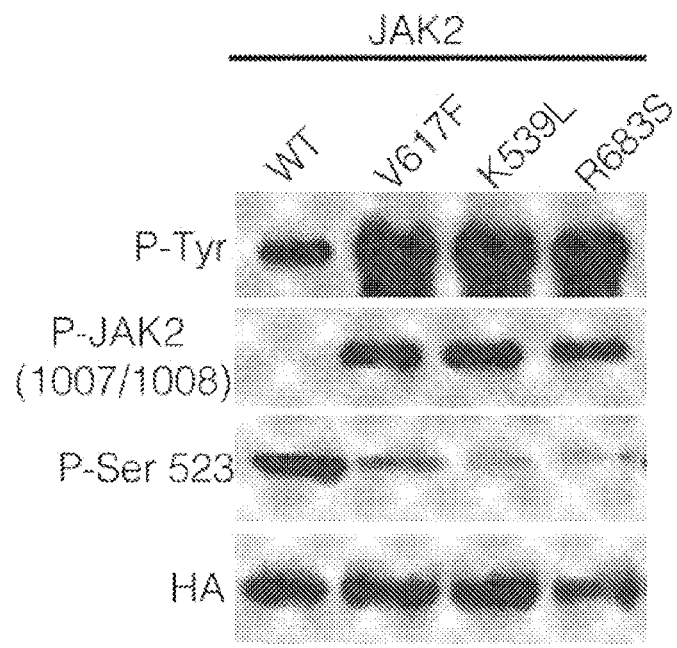

FIG. 17 is an immunoblot demonstrating phosphorylation of different JAK2 MPN mutants. JAK2WT and different MPN-mutants were transfected in γ2A cells. JAK2 protein was immunoprecipitated with anti-HA antibody and immunoblotted with anti-pJAK2 (1007/1008) and anti-pSer523. Equal protein levels loading were verified by anti-HA immunoblot.

Figure 18:
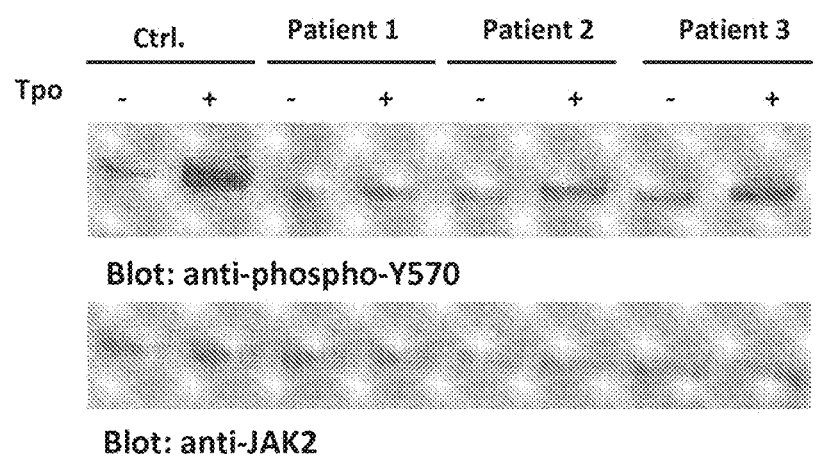

FIG. 18 is an immunoblot demonstrating the tyrosine 570 phosphorylation levels of JAK2 in MPN patient cells. Platelets were isolated from a healthy control and three MPN patients carrying V617F mutation. Cells were stimulated with Thrombopoietin (Tpo) and phosphorylation of Tyr570 was analysed immunoblotting. JAK2 protein levels were determined by immunoblotting.

DETAILED DESCRIPTION OF THE INVENTION

The present invention is based on an unexpected finding that, against well established consensus in the field, the JH2 domain of JAK proteins is catalytically active. Based on the present findings, the JH2 domain is an activate protein kinase that may possess both tyrosine kinase activity and serine kinase activity.

Furthermore, it has now been found that catalytic inactivation of JH2 domain, e.g. by an inactivating mutation K581A, K581R or N678A in JH2 of JAK-2, abolishes aberrant activation of JAK signaling caused by activating point mutations, such as V617F. Thus, JH2 domain plays a crucial role in regulating JAK signaling, and especially contributes to aberrant, disease causing hyperactivity of JAK signaling. JH2 is, thus, a true and important target for drug development, especially for myeloproliferative neoplasms and leukemias as well as for immunological and autoimmune diseases, metabolic, cardiac and neurological diseases, inflammatory and viral diseases. This invention thus provides means to develop mutation and disease specific modulators for JAK kinases, that may target mutated or wild type JAK kinases.

The term "JAK protein" refers to any member of the Janus kinase protein family or orthologous proteins in different species. In mammals, the JAK family consists of four members, i.e. JAK1 (SEQ ID NO. 1), JAK2 (SEQ ID NO. 2), JAK3 (SEQ ID NO. 3), or TYK2 (SEQ ID NO. 4). The term "JAK protein" includes catalytically active conservative sequence variants thereof, as well as catalytically active proteins having a sequence identity of at least 85%, 90%, 95%, 96%, 97%, 98% or 99% with a given JAK sequence.

Presumed amino acid boundaries of the JH2 domains are based on protein kinase sequence alignments and homology predictions. Thus, the boundaries may not be precise as no structure of the JAK domains exists except for tyrosine kinase domain JH1. It is generally accepted that in mammals the JH2 domain of JAK1 consists of amino acids 583-845 of SEQ ID NO. 1, whereas the JH2 domain of JAK2 consists of amino acids 545-805 of SEQ ID NO. 2, the JH2 domain of JAK3 consists of amino acids 521-777 of SEQ ID NO. 3, and JH2 domain of TYK2 consists of amino acids 589-866 of SEQ ID NO. 4.

As used herein, the term "catalytically active JH2 domain" includes catalytically active conservative sequence variants, as well as catalytically active JH2 domains having a sequence identity of at least 85%, 90%, 95%, 96%, 97%, 98% or 99% with a given catalytically active JH2 sequence.

The catalytic activity and solubility of different JH2 containing constructs were analysed in connection with the present invention. A JAK2 construct containing nine additional N-terminal amino acids to the predicted JH2 domain (i.e. starting from amino acid 536 of SEQ ID NO. 2) was found to be poorly soluble. The mutation of Val 617 to Phe increased the solubility of the 536-827 JH2 domain. It was further found out that phosphorylation of Ser523 lying outside the predicted JH2 boundaries stabilized the autophosphorylation activity of JH2. Wild type JH2 constructs (JH2WT; amino acids 513-827 of SEQ ID NO. 2) were found to be soluble as well as catalytically active. Thus, in addition to amino acids 545-805 of SEQ ID NO. 2, the JAK2 JH2 domain requires further N-terminal amino acids, preferably at least nine, preferably at least 22, and more preferably at least 32 N-terminal amino acids for its catalytic activity.

Similar results were obtained with JH2 domains of JAK3. A construct containing nine additional N-terminal amino acids to the predicted JH2 domain was catalytically active. Based on the present findings, active JH2 domain of JAK3 requires in addition to amino acids 521-777 of SEQ ID NO. 3 further N-terminal amino acids, preferably at least nine amino acids. In some embodiments, catalytically active JH2 comprises amino acids 512-800 of SEQ ID NO. 3.

The active JH2 domain of JAK1 may contain additional eight, or 16 or 30 amino acids to its N-terminus site, the catalytic active JH2 of JAK1 thus comprising amino acids 553-856, 567-856 or 574-856 of SEQ ID NO. 1. The active JH2 domain of TYK2, in turn, may contain 12, 18 or 25 additional N-terminal amino acids, thus comprising amino acids 564-876, 577-876, or 571-876 of SEQ ID NO. 4.

The catalytic activity of isolated and purified JH2 domain of JAK proteins was demonstrated by experimental studies showing that the JH2 domain is capable of binding ATP and catalyzing autophosphorylation of tyrosine and serine residues as well as substrate transphosphorylation. The tyrosine kinase activity of JH2 was found to have strong preference for $Mn^{2+}$ as a cation. This is an unexpected feature since almost all other kinases are dependent on $Mg^{2+}$. Results obtained from in vivo studies confirmed the tyrosine kinase activity of the JH2 domain.

It was further found out that the JH2 domain of JAK2 regulates the phosphorylation of Ser523 lying outside the predicted JH2 boundaries. The results also show that phosphorylation of Ser523 is important for JH2 activity. Relevant to these findings is that previous studies have identified both Ser523 and Tyr570 as negative regulatory sites for JAK2 activity. Importantly, the Ser523 phosphorylation is abrogated by a JH2 inactivating K581A mutation in a JH2 domain of a full length JAK2. Furthermore, V617F mutation, as well as two other MPN causing mutations, K539L (exon 12) and R683S (exon 16), in JH2 domain cause downregulation of Ser523 phosphorylation, indicating this as a mechanism for increased activation of JAK2 by V617F mutation. These three mutations represent well the JH2 mutations in JAK2 as they reside in the three mutational hotspots in the JH2 domain. In addition, Ser523 and Tyr 570 phosphorylations can be applied as biomarkers for MPN diseases and its progression and therapeutic response. These and other results obtained in connection with the present invention indicate that the catalytic activity of JH2 domain critically regulates the activation and signaling of JAK2, and especially that modulators of JH2 catalytic activity function as potent inhibitors of mutated, aberrantly activated JAK molecules. These findings have been exemplified with the V617F JAK2 mutant, but the principle is applicable also to other JAK2, JAK3, JAK1, and TYK2 mutations and aberrantly activated forms of these kinases. The results demonstrating that inactivation of JH2 domain in JAK3 by K556A mutation affects IL-2 induced signaling provide additional proof for the concept of JH2 targeting as a means to modulate cytokine signaling.

The present findings open a whole new approach for the development of JAK specific medicaments, especially for treating, preventing and/or alleviating diseases or conditions associated with hyperactive JAK signaling. Point mutations causing constitutively active, i.e. hyper-activating, JAK signaling include, but are not limited to, JAK2-V617F, JAK2-M531I, JAK2-F537I, JAK2-K539L, JAK2-F537-K539delinsL, JAK2-H538QK539L, JAK2-H538D+K539L+I546S, JAK2-H538-K539del, JAK2-D620E, JAK2-V617FD629E, JAK2-V617FC618R, and JAK2-V617FC616Y causing myeloproliferative disorders; and JAK2-L611S, JAK2-K607N, JAK2-T875N, JAK3-A572V, JAK3-A573V, JAK3-A593T+A573V. JAK3-V722I, JAK3-P123T, JAK1-T478S, JAK1-V623A, JAK1-A634D, JAK1-V658F, JAK1-R724H, and JAK1-L683F. Other activating JAK mutations are known to a person skilled in the art.

Further, JH2 modulators can be applied as therapies in diseases where JAK kinases are not mutated but mediate pathogenic signaling. For instance, JAK kinases are activated without known genetic alterations in several human diseases such as tumors, allergic and autoimmune diseases, inflammation and infectious diseases, stroke, heart diseases such as infarction and myocardial dilation, diseases of metabolic and neural systems, as known to a person skilled in the art. These diseases pose an important target for modulators of JH2 in JAK kinases.

An important aspect of this invention is the dual role of JH2 domain in regulation of cytokine signalling. Thus, JH2 modulators may inhibit or activate JH2 activity, and consequently increase or decrease cytokine signalling. Results exemplified in FIG. 13 and FIG. 16 provide evidence for this aspect by showing that inactivation of JH2 activity in JAK2 increases the basal activity and signalling of normal JAK2 but restore normal regulation of mutated V617F JAK2. These results indicate that JH2 inhibitors may be used also for increasing JAK and cytokine signalling in question, which is beneficial in various conditions such as anemia or deficiency of other blood cells, or where the immune response need to enhanced. In other words, JH2 modulators can be used to boost the JAK activation in conditions where this is desirable, such as anemia. Other such conditions and diseases are known to a person skilled in the art.

Thus, in one aspect the present invention provides a method or assay for screening and identifying modulators of JH2 kinase activity, as well as the use of a catalytically active JH2 domain of a JAK protein in said assay or method. Herein, the terms method and assay are used interchangeably, unless otherwise indicated. In some embodiments, the JH2 domain may be used alone or in combination with other JAK domains, such as JH1, or it may be comprised in a full length JAK protein. In other embodiments, the JH2 domain may comprise one or more hyperactivating mutations, such as those listed above. In further embodiments, the JH2 domain may lack catalytic activity.

The term "modulate" refers to either inhibition or activation of the kinase activity of JH2 and thus inhibition or activation of JAK/cytokine signaling and biological responses resulting therefrom. Furthermore, the term includes allosteric regulation of JH1 activity via JH2. The term "modulator" refers to any compound having said ability to modulate JH2. The term "inhibitor" refers to a compound inhibiting, inactivating or blocking the catalytic activity of JH2. Preferably, the inhibition results in complete blocking of said catalytic activity but also partial inhibition of the catalytic activity is encompassed by the present embodiments. The inhibitor of JH2 may activate or inhibit the activity of JH1 and cytokine signaling. Likewise, the term "activator" refers to a compound activating or enhancing the catalytic activity of JH2 compared to the level of said catalytic activity in the absence of said stimulator. In some specific cases, an inhibitor of JH2 activity may be an activator of JH1 activity, and an activator of JH2 may be an inhibitor of JH1.

As defined herein, the term "allosteric modulator" or "allosteric regulator refers to a compound which can allosterically modulate JAK activity. The binding of an allosteric modulator occurs at a binding site distinct from the active site, resulting in a conformational change which influences protein function. A catalytically inactive JH2 domain may be used especially for screening and identifying allosteric modulators of JAK activity.

Isolated and purified JH2 domains may be obtained by standard recombinant methods. A desired JH2 domain may be cloned into a suitable expression vector and expressed in a compatible host according to methods well known in the art. Examples of suitable hosts include but are not limited to bacteria (such as *E. coli*), yeast (such as *S. cerevisiae*), insect cells (such as SF9 cells), and mammalian cell lines. Expression tags, such as His-tags, hemagglutinin epitopes (HA-tags) or glutathione-S-transferase epitopes (GST-tags), may be used to facilitate the purification of the JH2 domain.

The assay for screening and identifying modulators of JH2 signaling may be based on detecting tyrosine phosphorylation, including but not limited to Tyr570, and/or serine phosphorylation, including but not limited to Ser523 phosphorylation of JAK2. In some embodiments, the assay is based on the effect of a test compound on the ability of a JAK polypeptide comprising a catalytically active JH2 domain to undergo autophosphorylation.

In an autophosphorylation assay, a test compound suspected of being a modulator of JH2 activity is contacted or reacted with a suitable reaction mixture comprising isolated and purified JAK polypeptide comprising a JH2 domain as a source of tyrosine or serine kinase activity under conditions and for a time sufficient to allow phosphorylation of a tyrosine and/or serine residue. The tyrosine kinase reaction may be initiated in the presence of ATP or an analog thereof and $Mn^{2+}$ or $Mg^{2+}$ (e.g. as $MnCl_2$ or a mixture of divalent cations comprising $Mn^{2+}$ or $Mg^{2+}$), whereas the serine kinase reaction may be initiated in the presence of ATP and divalent cations, such as $Mn^{2+}$ (e.g. as $MnCl_2$ or a mixture of divalent cations comprising $Mn^{2+}$) or $Mg^{2+}$ (e.g. as $MgCl_2$ or a mixture of divalent cations comprising $Mg^{2+}$), or mixtures thereof.

Subsequently, the presence or absence of autophosphorylated tyrosine and/or serine residues may be determined by standard methods known in the art. Such methods include, but are not limited to mass spectrometry, microscopy, spectroscopy, western blotting, and immunoassays such as SPR, RIA, EIA and ELISA wherein phosphotyrosine or phosphoserine specific antibodies (including polyclonal, monoclonal, chimeric and single chain antibodies as well as FAb fragments) available in the art may be used. The antibody may be directly or indirectly labelled e.g. with a radiolabel, fluorescent label, luminescent label, or enzymatic label capable of producing a detectable signal.

The assay may comprise a step, wherein the level of serine and/or tyrosine phosphorylation of JH2 in the presence of a test substance is compared to that in the absence of said test substance. If the level of serine and/or tyrosine phosphorylation is increased as compared to the control (no test substance present), the test substance is regarded as an activator of JH2 kinase activity. On the other hand, if the level of serine and/or tyrosine phosphorylation is decreased as compared to the control, the test substance is regarded as an inhibitor of JH2 kinase activity. It should be noted that an inhibitor of JH2 may act as an activator for JH1 activity and signaling, and in some specific embodiments the inhibitor may inhibit JH1 activity and signaling.

In some embodiments, the level of JH2 autophosphorylation of JAK2 may be determined with an antibody directed against phosphorylated Tyr570 (disclosed e.g. in Feener et al., Mol. Cell. Biol. 2004, 24: 4968-4978) and/or an antibody directed against phosphorylated Ser523.

In other embodiments, the assay is based on the capability of a test compound to modulate the ability of JH2 to bind substrate or transphosphorylate tyrosine and/or serine residues of a substrate. Herein, the term "substrate" refers to a protein or a peptide which is acted on by the tyrosine and/or serine kinase activity of JH2 such that it is phosphorylated on tyrosine and/or serine residues, respectively.

In a transphosphorylation assay, a test compound suspected of being a modulator of JH2 activity is contacted or reacted with a suitable reaction mixture comprising isolated and purified JAK polypeptide comprising a catalytically active JH2 domain as a source of tyrosine and/or serine kinase activity and a substrate. Suitable tyrosine substrates are available in the art and include, but are not limited to, Poly-Gly-Tyr peptide and peptides or proteins comprising Tyr570. Suitable serine substrates are also available in the art and include, but are not limited to, peptides or proteins containing Ser523 residues of JAK2. The kinase reaction is initiated in the presence of ATP and divalent cations such as $Mn^{2+}$ or $Mg^{2+}$ as described above. The reaction is carried out under conditions and for a time sufficient to allow phosphorylation of a tyrosine and/or serine residue. Subsequently, the presence or absence of phosphorylated tyrosine and/or serine residues in the substrate may be determined by standard methods known in the art as described above for autophosphorylation assays. Further, the assay may comprise a step, wherein the level of transphosphorylation in the presence of a test substance is compared to that in the absence of said test substance. If the level of serine and/or tyrosine transphosphorylation is increased as compared to the control (no test substance present), the test substance is regarded as an activator of JH2 kinase activity. On the other hand, if the level of serine and/or tyrosine transphosphorylation is decreased as compared to the control, the test substance is regarded as an inhibitor of JH2 kinase activity.

In the above assays, the substrate may be immobilised on a solid surface such as a microtiter plate allowing high throughput screening and automation of the assay. Means and methods for immobilizing substrates are available in the art. In other embodiments, the JH2 domain (or JH1+JH2 domain, or full-length JAK) may be immobilized to said solid surface. This applies to all embodiments of the screening and identification assay disclosed herein.

Allosteric modulators of JAK activity may be screened and identified in assays, for instance, wherein JAK proteins comprising both JH1 and JH2 domains are used as a source of kinase activity. In such embodiments, wherein tyrosine kinase activity is to be determined, the assay is performed as described above with the exception that the readout is based on detection of the activation of JH1 domain, for example by detection of phosphorylated activation loop tyrosine residues in JH1 domain. Test substances are determined as allosteric modulators of JH2 tyrosine kinase activity if the compound does not bind the kinase active site of JH2 and if the level of JH2 activity and/or JH1 activation loop tyrosines phosphorylation is altered in JH1+JH2 constructs but not in JH1 constructs lacking JH2 domain. Specific antibodies for determining the phosphorylation of activation loop tyrosines of different JAK proteins are commercially available. Instead, in such embodiments, wherein serine kinase activity is to be determined, the assay is performed as described above with the exception that the readout is based on detection of the phosphorylation of Ser523 or other serine containing peptides or proteins. Test substances are determined as allosteric modulators of JH2 serine kinase activity if the compound does not bind to the active site of JH2 domain and the level of Ser523 or other Ser residue phosphorylation is altered. Specific antibodies for determining the Ser523 phosphorylation have been reported in the literature. Examples of suitable JH1+JH2 constructs include those comprising activation loop tyrosines of JH1, i.e. amino acids Tyr1007/1008 of JAK2 or Tyr980/981 of JAK3, Tyr 1034/1035 of JAK1 and Tyr1054/1055 of Tyk2, as well as those comprising Ser523 of JAK2.

The JH2 domain used in various embodiments of the present assay may consist of amino acids selected from a group consisting of amino acids 513-827 of SEQ ID NO. 2, amino acids 523-827 of SEQ ID NO. 2, amino acids 521-777 or 512-800 of SEQ ID NO. 3, amino acids 553-856, 567-856 or 574-856 of SEQ ID NO. 1, and amino acids 564-876, 577-876, or 571-876 of SEQ ID NO. 4. In still some other embodiments, full length JAK polypeptide or JAK polypeptides lacking defined regions may be used for screening and identifying modulators of JH2 signaling.

In all the above assays, proteins comprising wild type JH2 or proteins harbouring mutated JH2 domain may be used. The choice of the JH2 domain depends on the purpose of the assay as readily understood by a person skilled in the art. For example, comparison between wild type and mutated forms allows identification of disease specific modulators.

In the case of mutated JH2 domain, the assay for screening and identifying modulators of JH2 signaling may be based on detecting phosphorylation of any residue of a JAK polypeptide, including phosphorylation of tyrosine residues, such as Tyr570, and phosphorylation of serine residues, such as Ser523. Such assays may be based on autophosphorylation or transphosphorylation as described above. The mutated JH2 domain may be used alone or in combination with other JAK domains, such as JH1, or it may be comprised in a full length JAK protein.

Thus, the assay for screening and identifying modulators of JH2 kinase activity may comprise the steps of: a) reacting a test substance with a reaction mixture comprising a hyperactive, mutated JAK polypeptide comprising a JH2 domain, ATP or an analog thereof, and divalent cations under conditions and for a time sufficient to allow phosphorylation of a tyrosine or serine residue, and b) determining the level of phosphorylation of JH2 domain in said reaction mixture, and c) identifying said test substance as modulator of JH2 kinase activity if the level of phosphorylation in step b) is different from the level of phosphorylation in the absence of said test substance. The assay may be based on competition, inhibition or enhancement of ATP binding to JH2, ADP production or phosphorylation of substrate/ligand of JH2.

In some embodiments, the JH2 domain comprises a V617F mutation or other disease causing mutations. Such assays are particularly suitable for screening and identifying compounds for treating, preventing, and/or alleviating MPNs such as PV, thrombocythemia ET, and idiopathic myelofibrosis IMF, immune deficiencies, autoimmune diseases, cancer, and leukemias, metabolic and neurological diseases.

In some embodiments, modulators of JH2 activity can also be screened, identified and characterized by employing calorimetric methods such as Differential Scanning calorimetry or Fluorimetry, or Isothermal Titration Calorimetry or Fluorimetry, where the binding of the modulator is analysed with respect to a change in the melting temperature Tm of JH2. Such methods are known to a person skilled in the art and include measurement of surface plasmon resonance or spectrocopical methods including fluorescence, UV/visible light, CD, NMR based methods and microscopy methods including atom force microscopy as well as crystallography.

In further embodiments, cell based assays may be used for screening and identifying modulators of JAK proteins. In such assays, the desired JH2 construct (full length or truncated JAK polypeptide with or without JAK activity modifying mutations) is expressed in a suitable expression vehicle in a cell line, preferentially in cells that lacks the specified JAK kinase (e.g. γ2A cells in the context of JAK2). The JAK constructs may be full length, include also N-terminus or other domains of the proteins and have either normal or inactivated JH1 domains. Receptor activation may be employed and the readout may be based on detection of tyrosine (e.g. Tyr570) or serine (e.g. Ser523) phosphorylation (in the context of JH2 activation) or JH1 activation loop tyrosines as described above or as activation of downstream signalling cascades/proteins such as STAT transcription factors, PI-3K/Akt cascade, MAP kinase pathway. Furthermore, colony formation, cellular mobility, proliferation and other cellular functions can be used as a readout for the assays. In some embodiments, a mutated or wild type JAK may be expressed in bone marrow cells and in which case the readout may be hematopoietic colony formation. In some other embodiments, a JAK polypeptide comprising disease causing mutations may be expressed in BaF3 cells and the effect of a test compound on cellular functions, such as proliferation, may be used to determine the potential of the test compound as a drug candidate.

In further embodiments, non-human in vivo models can be employed as test and screening models, which can be either prokaryotic or eukaryotic. The readout will depend on the model used but can involve development of an immunological disease or immune response, hematopoietic diseases or lineages, tumor, diseases of central or peripheral neural system, a metabolic or cardiac disease or physiological responses such as growth, development, reproduction and lactation. Although over-expressing a JAK protein comprising a catalytically active JH2 domain in a non-human animal is likely to cause pathological changes, such transgenic animals provide a valuable tool for elaborating the role of JH2 activity in various physiological and pathological situations, as well as for screening therapeutic drug candidates for severe and life-threatening human diseases lacking clinically approved treatment.

Modulators of JH2 activity may be tested in non-human in vivo models, such as mouse or other rodent models. Mutated or wild type JAK proteins or polypeptides may be expressed in bone marrow cells that may be used for transplanting and to reconstitute a recipient non-human animal. In the case of mutations causing myeloproliferative neoplasms (such as V617F or any equivalent mutation), the readout may lie in the development of increased hematocrit or platelet count or abnormal bone marrow and in the case of leukemia causing mutations, in the development of the indicated disease.

In other aspects, the present invention provides a kit for determining modulators of JH2 activity. Such a kit comprises a JAK polypeptide comprising a catalytically active form of a desired JH2 domain. The JAK polypeptide may consist of a JH2 domain or it may comprise JH2 in combination with other JAK domains, such as JH1 or FERM. In some preferred embodiments, the JH2 domain comprises a V617F or other disease causing mutation. In some other embodiments, the JH2 construct contained in the kit is a construct described above. Furthermore, the kit may comprise a suitable antibody for assessing the tyrosine and/or serine kinase activity of the JH2 domain and means for detecting binding of said antibody to the possibly phosphorylated tyrosine and/or serine residues. In some cases the kit may further comprise a substrate for JH2 catalysed phosphorylation. Any of the above components may be provided as immobilized on a solid support, such as a microtiter plate.

The present assays and kits may be used for screening and identifying test compounds such as drugs, natural and synthetic peptides or small organic or inorganic molecules for their ability to modulate the kinase activity of JH2.

The compounds identified by the present assays as modulators of JH2 activity may be used for treating, preventing and/or alleviating human diseases including, but not limited to, MPNs such as PV, thrombocythemia ET, and idiopathic myelofibrosis IMF, immune deficiencies, autoimmune diseases, metabolic, cardiac and neurological diseases, infectious diseases, cancer, and leukemias either as single regimen therapy or in combination with other treatments. Furthermore, the JH2 modulators may be used in the treatment of human pathologies associated with cytokine receptor e.g. growth hormone, leptin, and prolactin signalling. In other embodiments, JH2 modulators can used to enhance, stimulate or restore JAK signalling and biological or therapeutic or preventive (such as vaccination) responses.

Given the regulatory role of JH2 on the overall JAK kinase activity, either inhibition or activation of JH2 activity may be used as a therapeutic modality. For example, hyperactivating JH2 mutations of JAK2 and JAK3 have been associated with leukemias, whereas inactivating mutations have been identified in JH2 of JAK3 resulting in SCID. Furthermore, the present findings indicate that the point mutation V617F in JH2 of JAK2 causing PV affects the enzymatic activity of JH2. Furthermore, inactivation of JH2 catalytic activity in MPN mutant JAK2 decreases basal JAK2 activity and restores cytokine regulation to signalling. These results indicate that disease and mutant specific modulators of JH2 can be developed for treating human diseases.

All the above embodiments described for the screening and identification assay and use of the JH2 domain apply to the kit, and vice versa.

EXAMPLES

It will be obvious to a person skilled in the art that, as technology advances, the inventive concept can be implemented in various ways. The invention and its embodiments are not limited to the examples described below but may vary within the scope of the claims.

Example 1

Production of JH2 Domain

JAK2 proteins JH1-JH2-WT, JH1-JH2-V617F, JH2-WT, JH2-V617F, and JH1 were cloned into pFASTBAC1 vector with a C-terminal thrombin cleavable 6×His tag or N-terminal thrombin cleavable GST tag. SF9 cells (*Spodoptera frugiperda*) were infected with recombinant bacmid DNA containing JAK2 domains at cell density of $1 \times 10^6$ cells/mL for virus amplification. For protein production, cells were infected at $2 \times 10^6$ cells/mL with 10% viral supernatant for 48 hours. Cells were lysed in buffer containing 20 mM TRIS-HCl (ph 8.0), 500 mM NaCl, 15% glycerol and 20 mM imidazole, supplemented with protease inhibitors cocktail (Roche Diagnostics, Mannheim, Germany), sonicated and centrifuged 1 h at 14000×g. The supernatant was incubated with Ni-NTA beads for 2 hours with gentle rotation at 4° C. The beads were extensively washed and the fusion proteins were eluted with 250 mM imidazole. Fractions containing His-tag fusion proteins were pooled and dialyzed overnight in buffer containing 20 mM TRIS-HCl (ph 8.0), 500 mM NaCl, 15% glycerol and 5 mM DTT. Samples were concentrated and loaded onto a Superdex 75 (10/30 GL) gel filtration column equilibrated in 20 mM TRIS-HCl (ph 8.0), 150 mM NaCl, 10% glycerol and 5 mM DTT buffer. Purification of GST tagged constructs was carried out according to standard procedures. Finally, fractions containing JAK2 proteins were concentrated and analyzed by Western Blot with anti-phosphotyrosine (4G10), and -JAK2 and anti-pTyr1007-1008 JAK2 antibodies.

Figure 1:
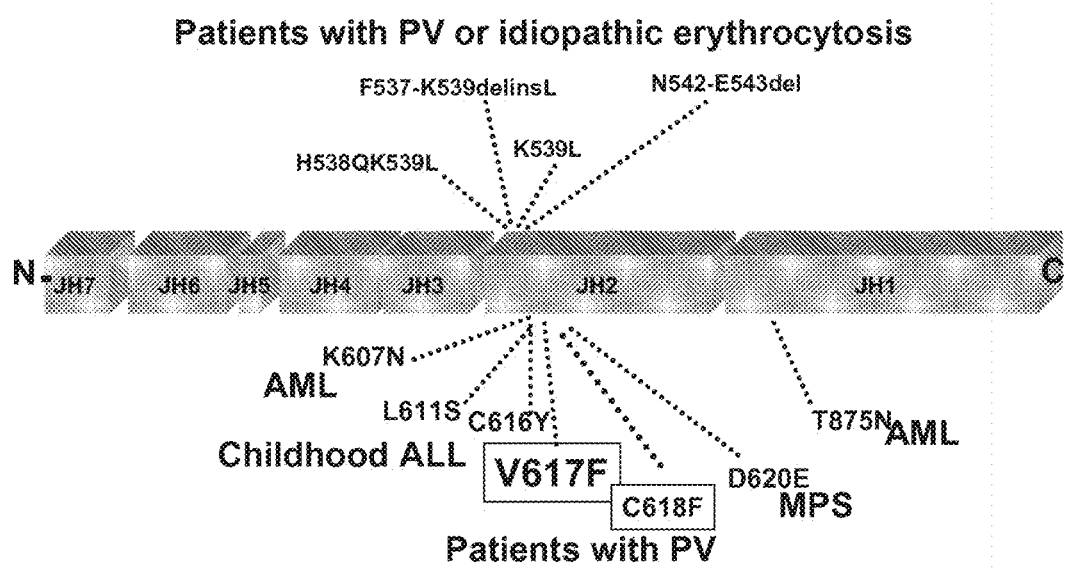
FIG. 1 is a schematic drawing of JAK protein structure. Point mutations associated with various human pathologies are shown. ALL, acute lymphoblastic leukemia; AML, acute myelogenous leukemia; PV, polycythemia vera (99% of PV patients have V617F mutation), MPS, myeloproliferative syndrome.
Figure 2:
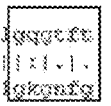
FIG. 2 shows an alignment of JH2 domain vs. JH1 domain of JAK2.
Figure 3:
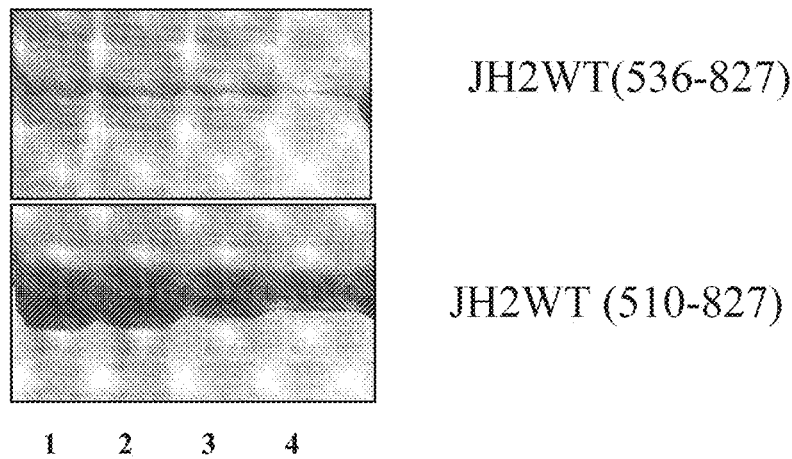
FIG. 3 shows JH2WT (536-827) and JH2WT (513-827) proteins of JAK2 produced and purified as described in Example 1. The proteins were eluted from Ni-NTA beads and separated on SDS-PAGE.

The expression and solubility of different JH2 containing constructs were analysed (FIG. 3). The construct starting close to the predicted JH2 domain (aa 536) was found to be poorly soluble. The mutation of Val 617 to Phe increased the solubility of the protein as 536 JH2 protein. The constructs containing Ser523 JH2WT (513-827) were found to be soluble and were used in subsequent activity analysis.

Figure 4:
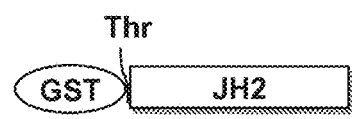
FIG. 4 illustrates JH2 domain constructs of JAK2 produced in baculovirus system and tested in chromatography.
Figure 4:
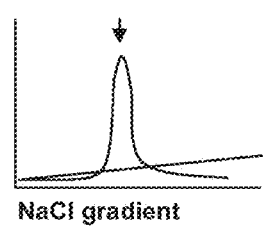
Figure 4:
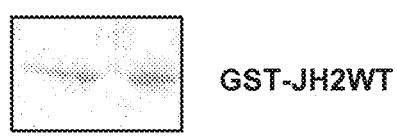

Next, the eluted soluble JH2 domains were analyzed on chromatogram and SDS-PAGE. The GST-tagged JH2 domain purified as a single peak (FIG. 4).

Example 2

In Vitro Activity of JH2 of JAK-2

The catalytic activity of JH2 was determined by in vitro kinase reaction and by immunoblotting with phosphospecific antibodies. To this end, cells were lysed in kinase lysis buffer (10 mM Tris-HCl, pH 7.5, 1% Triton X-100, 30% glycerol, 5 mM EDTA, 50 mM NaCl, 50 mM NaF, 1 mM $Na_3VO_4$) supplemented with protease inhibitors, and the lysates were purified using GST resin and used for immunoprecipitation with an anti-JAK2 antibody or directly for western blotting. The immunoprecipitation protocol has been described in Saharinen et al., Blood 1997, 90: 4341-4353. The immunoprecipitates were subjected to Western blotting or used for kinase assay.

For kinase assay, the immunoprecipitates were washed four times with kinase lysis buffer and twice with a kinase assay buffer (10 mM HEPES, pH 7.4, 50 mM NaCl, 50 mM NaF, 0.1 mM $Na_3VO_4$) containing 20 mM $MnCl_2$, or 20 mM $MgCl_2$, or 5 mM $MnCl_2$ and 5 mM $MgCl_2$. The immunoprecipitates were suspended in kinase assay buffer containing DTT (1 mM). 10 µCi [γ-$^{33}$P] ATP was added to the reactions followed by incubation at room temperature and the reactions were stopped by boiling in reducing Laemmli sample buffer at different time points. The reactions were separated in SDS-PAGE followed by quantification by autoradiography. The autoradiographs showed a time dependent increase in the JH2 autophosphorylation.

Figure 5:
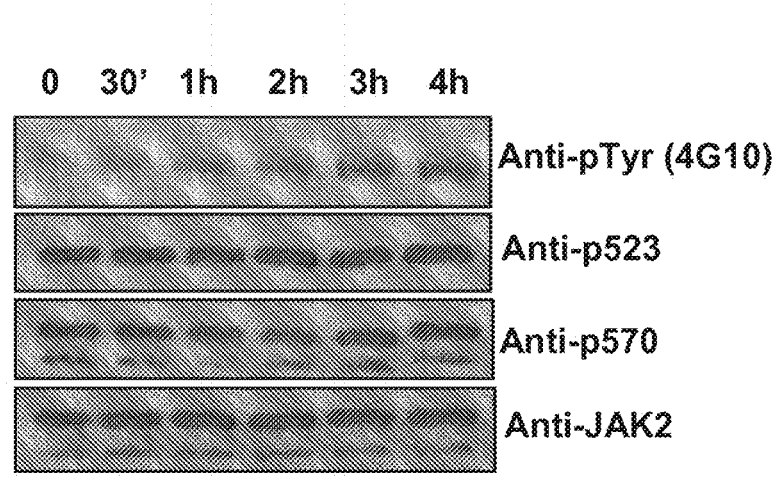
FIG. 5 is an immunoblot illustrating an in vitro kinase reaction using purified recombinant JH2 of JAK2, 10 mM ATP and 20 mM $MnCl_2$. Phosphorylation of JH2 was analyzed using anti-phosphotyrosine (4G10) antibody, anti-pSer523 antibody and anti-p570 antibody. JH2 protein levels were analyzed by stripping the membrane followed by anti-JAK2 Western Blot.

Equal amounts of protein from the cell lysates were always used for immunoprecipitations and Western blotting of the cell lysates. Protein concentrations were determined using the BioRad Protein Assay system (Bio-Rad Laboratories, Hercules, Calif.). Immunodetection was performed using specific primary antibodies, biotinylated anti-mouse Western Blot was done using anti-phosphotyrosine (4G10) antibody (Millipore), anti-pSer523 antibody (Ishida-Takahashi, Mol Cell Biol, 2006, 26, 4063-4073), anti-pTyr570 antibody (Feener et al., Mol. Cell. Biol. 2004, 24: 4968-4978), and anti-JAK2 antibodies (Silvennoinen, Proc Natl Acad Sci, 1993, 90, 8429-8435) diluted 1:1000 in TBS buffer, followed by secondary biotinylated anti-Mouse or anti-Rabbit antibodies (Dako-Denmark) diluted 1:3000 in TBS buffer and streptavidin-biotinylated horseradish peroxidase complex antibody (GE Healthcare) diluted 1:5000 in TBS buffer (FIG. 5). Anti-phosphotyrosine immunoblottings demonstrated that the autophosphorylated residues are tyrosines and that in the case of JAK2 said tyrosine is Tyr570.

Figure 6:
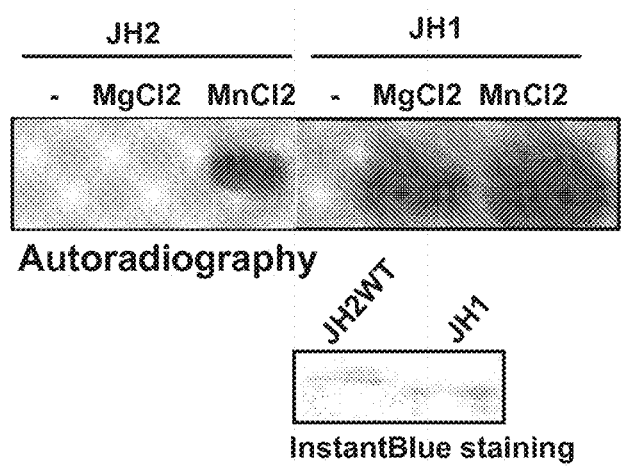
FIG. 6 is an autoradiograph illustrating in vitro ATP binding reactions for purified JH2 and JH1 domains of JAK2. Instant blue staining was used to control the protein levels in each blot.

Furthermore, the results showed that JH2 shows strong autophosphorylation in the presence of divalent cations and has a strong preference for $Mn^{2+}$ (FIG. 6).

Example 3

In Vitro Activity of JH2 of JAK-3

Figure 7:
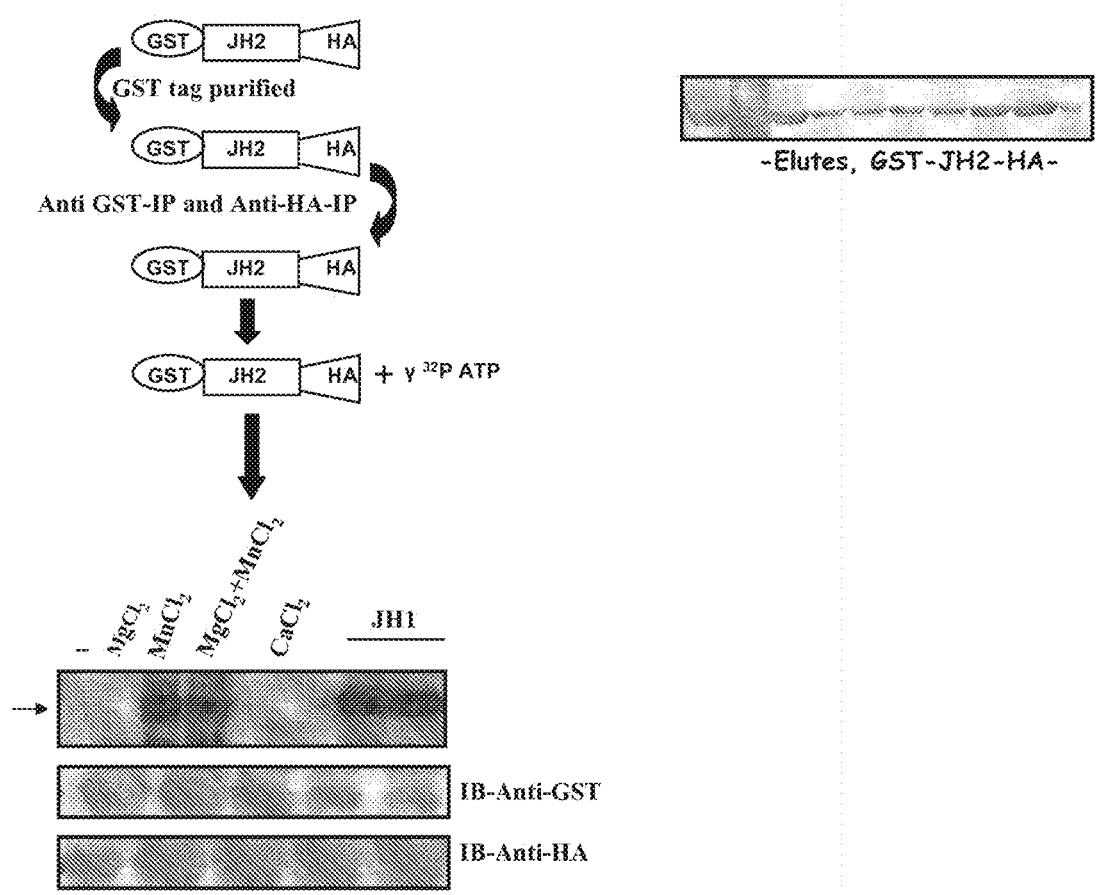
FIG. 7 shows a schematic drawing of JAK3 JH2 purification and an autoradiograph illustrating in vitro ATP binding reactions for purified JH2 and JH1 domains of JAK3. Immunoblotting with anti-GST and anti-HA antibodies were used for determining the protein levels.

The JH2 domain of JAK3 was produced and purified as in Example 1. The in vitro activity of JAK3 JH2 was analysed by in vitro autophosphorylation assay and Western blotting as in Example 2. Briefly, the JH2 domain of JAK3 (aa 512-800 of SEQ ID NO. 3) was produced in insect cells and subjected to anti-GST and anti-HA immunoaffinity purification. The results showed that JH2 has a strong kinase activity in the presence of $Mn^{2+}$ cations (FIG. 7). Similarly purified JH1 was used as a control.

Figure 8:
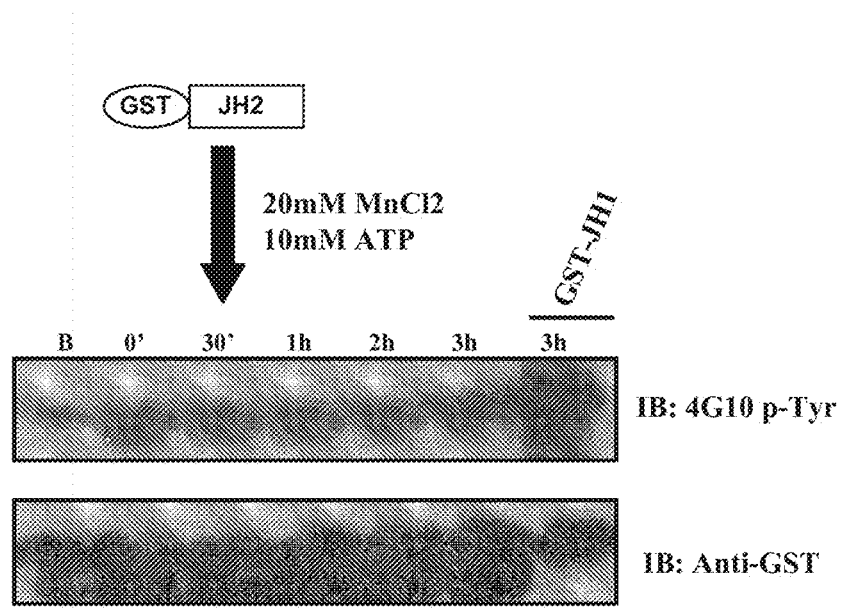
FIG. 8 is an immunoblot demonstrating that JH2 domain of JAK3 is tyrosine phosphorylated. Purified JH1 domain of JAK3 was used as a control for tyrosine phosphorylation.

Purified JH2 and JH1 domains of JAK3 were subjected to in vitro kinase reaction and blotting with an anti-pTyr antibody. The results showed that both JH1 and JH2 domains are tyrosine phosphorylated (FIG. 8).

Example 4

In Vitro Activity of JH2 of JAK-1

Figure 9:
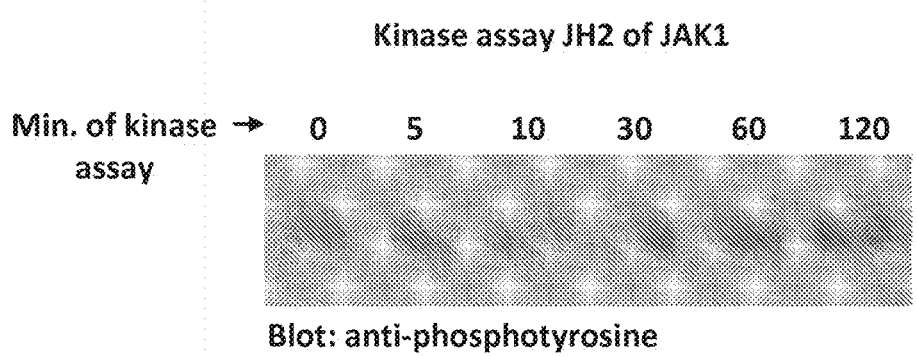
FIG. 9 is an anti-phosphotyrosine immunoblot demonstrating that purified JH2 domain of JAK1 is tyrosine phosphorylated.

The JH2 domain of JAK1 (aa 553-856 of SEQ ID NO. 1) was produced and purified as in Example 1. The in vitro activity of JAK1 JH2 was analysed by in vitro autophosphorylation assay and Western blotting as in Example 2. Briefly, the JH2 domain of JAK1 was produced in insect cells and subjected to anti-His immunoaffinity purification followed by gel-size chromatography purification. Purified protein was used at concentration 0.5 µM for an in vitro kinase assay and blotting with an anti-pTyr antibody. The results showed that JH2 is more autophosphorylated after 60 min and 120 min of kinase assay (FIG. 9).

Example 5

In Vitro Activity of JH2 of TYK2

Figure 10:
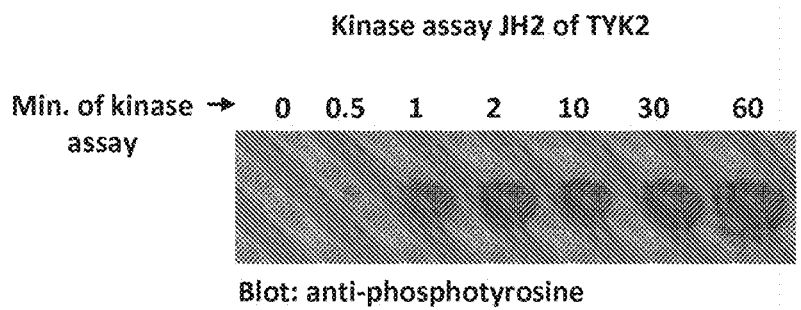
FIG. 10 is an anti-phosphotyrosine immunoblot demonstrating that purified JH2 domain of TYK2 is tyrosine phosphorylated.

The JH2 domain of TYK2 (aa 564-876 of SEQ ID NO. 4) was produced and purified as in Example 1. The in vitro activity of JAK1 JH2 was analysed by in vitro autophosphorylation assay and Western blotting as in Example 2. Briefly, the JH2 domain of TYK2 was produced in insect cells and subjected to anti-His immunoaffinity purification followed by anion-exchange chromatography purification. Purified protein was used at conc. 1 µM for an in vitro kinase assay and blotting with an anti-pTyr antibody. The results showed that JH2 becomes strongly autophosphorylated within 1 min of kinase assay (FIG. 10).

Example 6

In Vivo Catalytic Activity of JH2

Cell line and transfection γ2A (Jak2-deficient fibrosarcoma cell line) cells were grown on Dulbecco's modified Eagle's medium (Sigma) supplemented with 10% fetal bovine serum, 1 mM L-glutamine and antibiotics (100 U penicillin per ml, 100 µg of streptomycin per ml) and maintained at +37° C. in a humidified atmosphere containing 5% $CO_2$. The cells were transfected using FuGENE™ 6 transfection reagent (Roche Diagnostic, Indianapolis, Ind.) according to manufactures instructions. Day before transfection cells were plated in 6-well plates in the density of $0.2 \times 10^5$ per well in 2 ml of Dulbecco's modified Eagle's medium containing 10% fetal bovine serum, 1 mM L-glutamine and antibiotics. Cells were transiently transfected with 1 µg of HA-tagged JAK2-WT or JAK2ΔD1 (a construct lacking the JH1 domain) DNA plasmid together with 0.5 µg of hEpoR, depending on the experiment 6 h after transfection the media was changed into serum-free media and starved over night at +37° C., or left unstimulated. Following next day the cells were stimulated with Epo (30 U) (EPREX®, Janssen-Cilag Oy) for indicated time points at 37° C. After stimulation cells were wash once with ice-cold phosphate buffered saline and lysed in Triton-X lysis buffer (50 mM Tris pH 7.5, 10% glycerol, 150 mM NaCl, 1 mM EDTA, 1% Triton X-100) supplemented with protease inhibitors (2 mM $Na_3VO_4$, 1 mM PMSF, 8 µg/ml aprotin, 4 µg/ml pepstatin a) for 30 minutes followed by the centrifugation at 16 000 g for 20 minutes.

For immunoprecipitation cell lysates were incubated with monoclonal anti-HA antibody for 2 h at +4° C. rotating followed by incubation with protein G sepharose for 1 h at 4° C. rotating. Samples were washed twice with kinase buffer and eluted with equal amount of 2×SDS sample buffer, boiled for 5 minutes and centrifuged at 13 000 g for 1 minute. Immunoprecipitated samples and lysates were resolved by 6% SDS-polyacrylamide gel and transferred to nitrocellulose membrane. Immunodetection was carried out using specific primary antibodies, biotinylated secondary antibodies (DAKO A/S) and streptavidin-biotin horseradish peroxidase-conjugate (Amersham Biosciences AB) followed by ECL. Following primary antibodies were used: anti-hemagglutinin (anti-HA, Berkley-Antibody, Richamond, Calif., USA), anti-phosphotyrosine (clone 4G10, Zymed laboratories Inc. San Francisco, Calif., USA), and anti-pTyr570 (Feener et al., Mol. Cell. Biol. 2004, 24: 4968-4978). The anti-HA immunoblot was used to determine the protein levels.

Figure 11:
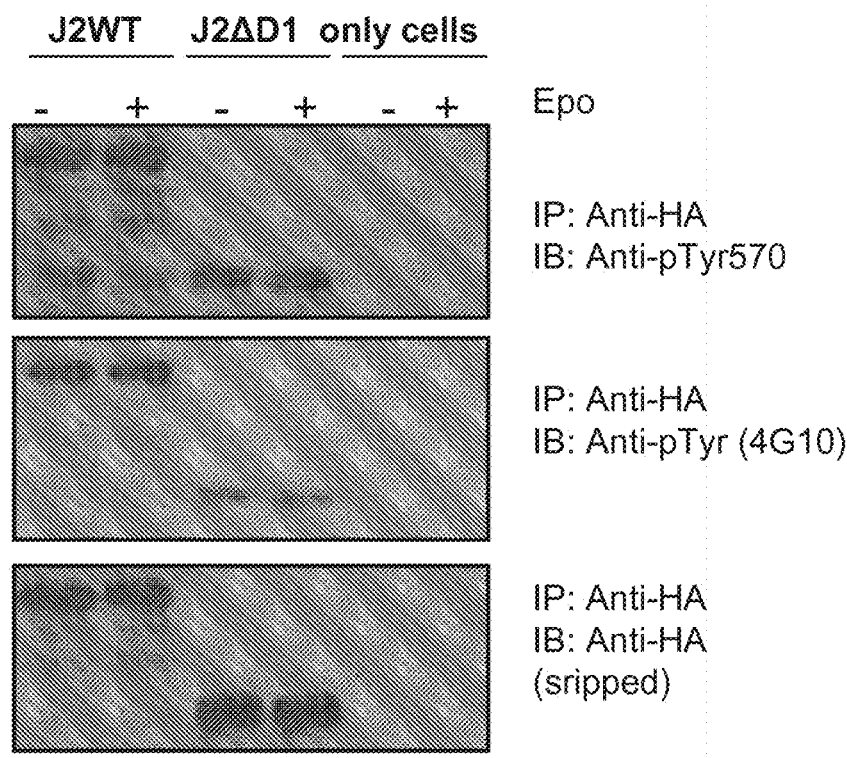
FIG. 11 is an immunoblot demonstrating that JH2 of JAK2 is tyrosine phosphorylated in cells. HA-tagged JAK2-WT and JAK2ΔD1 (a construct lacking JH1 domain) proteins from transfected γ2A cells were immunoprecipitated (IB) with an anti-HA antibody and Western blotted (IB) with anti-pTyr570 or anti-pTyr (4G10) antibodies. Immunoblotting with anti-HA antibody was used for determining the protein levels after stripping.

FIG. 11 shows that JAK2 protein which lacks the JH1 tyrosine kinase domain becomes tyrosine phosphorylated in cells which lack endogenous JAK2. Anti-pTyr570 blotting demonstrated that Tyr570 is the autophosphorylation site for the JH2 domain. In other experiments, tyrosine phosphorylation of JAK2ΔD1 was increased by Epo stimulation.

Example 7

JH2 Catalytic Activity is Required for Ser523 Phosphorylation

Figure 12:
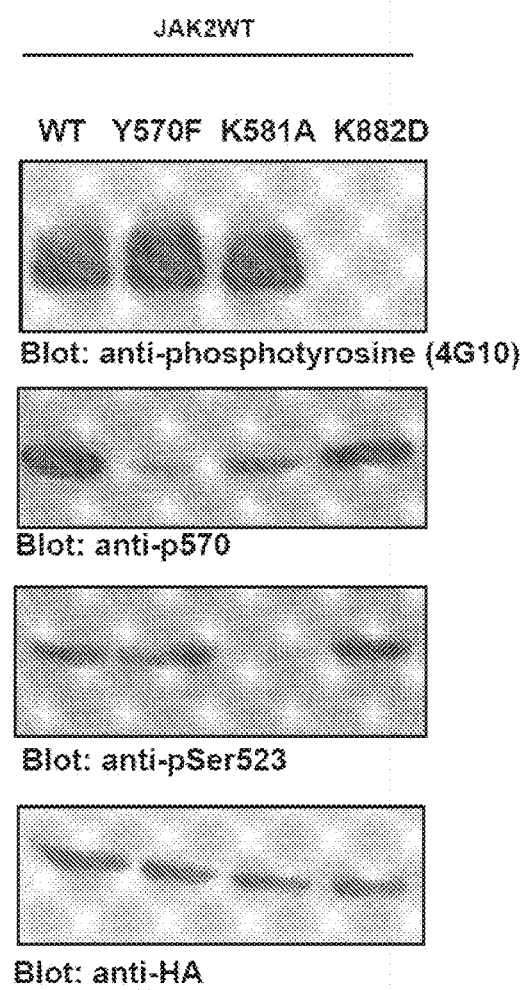
FIG. 12 is an immunoblot demonstrating that JH2 domain regulates serine phosphorylation of JAK proteins in cells.

Human γ2A cells (lacking JAK2) were transfected with HA-tagged full length JAK2 constructs (JAK2WT, JAK2Y570F, JAK2K581A, JAK2K882D). Proteins were immunoprecipitated with anti-HA antibody and immunoprecipitates were resolved on 6% SDS-page and analyzed by anti-pTyr(4G10), anti-pTyr570 and anti-Ser523 antibodies. Protein levels were determined by anti-HA immunoblot (FIG. 12).

The results show that mutation of either negative regulatory site Y570 or the ATP coordinating K581 of the JH2 domain result in increased tyrosine phosphorylation of JAK2. Further, the results show that K581A mutation abrogates Ser523 and Ty570 phosphorylation. Importantly, mutation of the ATP coordinating lysine K882 in the tyrosine kinase domain (JH1) does not affect Y570 or S523 phosphorylations.

Example 8

Inactivation of JH2 Catalytic Activity Inhibits the Aberrant Signaling by V617F Mutant JAK2

Human γ2A cells (lacking JAK2) were transfected with HA-tagged full length wild type or V617F mutant JAK2 constructs (JAK2WT, JAK2WTY570F, JAK2WTK581A, JAK2VF, JAK2VFY570F, JAK2VFK581A). Proteins were immunoprecipitated with anti-HA antibody and immunoprecipitates were resolved on 6% SDS-page and analyzed by anti-phosphoJAK2 (Y1007/8), anti-pTyr(4G10), anti-Ser523, and anti-Tyr570 antibodies. Protein levels were determined by anti-HA immunoblot (FIGS. 13 and 14).

The results show that in the context of wild type JAK2, mutation of either negative regulatory site Y570 or the ATP coordinating K581 result in increased tyrosine phosphorylation of JAK2 on activation loop tyrosines Y1007/8. In the context of JAK2V617F, mutation of regulatory Y570 did not affect the activation status as measured by Y1007/8 phosphorylation. Importantly, mutation of JH2 K581 dramatically decreased the activation of JAK2. Additional novel finding is that JAK2V617F shows strongly decreased Ser523 phosphorylation.

The results prove that in the context of full-length JAK, inactivation of JH2 catalytic activity inhibits aberrant, disease causing JAK2 signaling in cells. Catalytically active JH2 domain is thus a relevant drug target, especially for diseases involving aberrant JAK signaling.

Example 9

JH2 Regulates Downstream Signaling of Aberrantly Activated JAK2 as Measured by STAT1 Phosphorylation and in Human γ2A cells (lacking JAK2) were transfected with HA-tagged full length wild type or V617F mutant JAK2 constructs (JAK2WT, JAK2VF JAK2VFK581A) together with STAT1 expression construct. Cells were starved overnight and stimulated with IFN-gamma, or left unstimulated. Cell lysates were resolved with 6% SDS-page and analyzed with anti-phospho-STAT1 antibody (FIG. 15).

The results show that expression of wild type JAK2 results in STAT tyrosine phosphorylation. Expression of JAK2V617F results in enhanced STAT1 tyrosine phosphorylation. However, mutation of the ATP coordinating K581A results in decreased STAT1 tyrosine phosphorylation demonstrating that the inactivation of JH2 catalytic activity in JAK2V617F decreases aberrant downstream signaling.

Example 10

JH2 Mutations Affect the Activity of JH1

FIG. 16A shows an immunoblot demonstrating tyrosine phosphorylation of STAT1 in response to IFN-γ stimulation, whereas FIG. 16B shows an immunoblot demonstrating that of STAT5 in response to erythropoietin (Epo) stimulation. HA-tagged full length wild type (JAK2WT), and JAK2 Y570F and JAK2K581A mutants together with STAT1 or STAT5 construct, respectively, were expressed in γ2A cells and after 8 h cells were starved for 12 h in serum-free media followed by stimulation with hIFN-γ (100 U/ml) or hEpo (50 U/ml). After cell lysis, STAT1 phosphorylation was analysed by Western Blotting with anti-pSTAT1 antibody or anti-pSTAT5 antibody.

FIG. 16C shows the effect of JAK2 K581A mutation on STAT1 transcription activation using IFN-γ-dependent GAS luciferase reporter (Mean±SD, n=3), whereas FIG. 16D shows the effect of JAK2 K581A mutation on STAT5 transcription activation using SPI-Luc2 luciferase reporter (Mean±SD, n=3).

The results show that inactivation of JH2 by K581A mutation increases basal activity and signalling of JAK2. Compared to JAK2 WT, JAK2K581A, as well as mutants of JH2 substrate residues Ser523 and Tyr570, increased basal phosphorylation of STAT1 and STAT5. These findings were observed also in functional STAT1- and STAT5-mediated transcriptional responses.

FIG. 17 is an immunoblot demonstrating phosphorylation of different JAK2 MPN mutants. JAK2 WT and JAK2 MPN-mutants were transfected in JAK2-deficient γ2A cells. JAK2 protein was immunoprecipitated with anti-HA antibody and immunoblotted with anti-pJAK2 (1007/1008) and anti-pSer523. Equal protein levels loading were verified by anti-HA immunoblot.

The results show that three MPN JAK 2 mutants, representing the mutational hotspots in JH2 domain (K539L exon 12, V617F exon 14, R683S exon 16), all increase basal JAK2 activity (Tyr1007/1008 phosphorylation) and inhibit phosphorylation of inhibitory residue Ser523. As Ser523 is a substrate for JH2, the result indicates that the MNP mutations cause abrogation of JH2 activity.

Example 11

In Vivo Studies

In vivo models, such as rodents, are used to identify and test JH2 targeting compounds and modulators, both inhibitors and activators. A JAK kinase sequence, either disease causing or wild type, is expressed in the animal. This is achieved by transplanting bone marrow cells that are transduced to express ((e.g. by retroviral infection, or plasmid transfection) the named JAK sequence into a recipient animal, e.g. an irradiated or otherwise immunocompromised or depleted of hematopoietic cells. Alternatively, the expression of the JAK sequence is achieved by standard genetic targeting methods such as knock in, transgene expression, or knock out approaches known to a person skilled in the art. The readout depends on the JAK and mutation used, but can be e.g. hematocrit, development of tumour, immunological disease, neurological disease, altered metabolism or analysis of JAK, or JAK regulated proteins modifications such as phosphorylation, localization or activation status.

Introduction of the V617F mutation in combination with the JH2 inactivating K581A mutation into a mouse results in decreased hematocrit as compared to that of a mouse introduced with a V617F mutation only.

Thus, these experiments show that inactivation of JH2 inhibits the disease phenotype in vivo.

12. Patient Studies

Altered JH2 function was also observed in clinical samples from MPN patients. Platelets were isolated from a healthy control and 3 different patients diagnosed with PV and left unstimulated or stimulated with Tpo (100 ng/ml) for 15 min at room temperature. Equal amounts of protein were run on SDS-page gels. The expression of JAK2 allele among different patients was as following:

Patient 1: PV, JAK2-V617F allelic ratio: 95%
Patient 2: PV, JAK2-V617F allelic ratio: 72%
Patient 3: PV, JAK2-V617F allelic ratio: 71%

As a readout for JH2 activity, the phosphorylation of JAK2 Y570 was analyzed. Tpo stimulation readily induced Y570 phosphorylation in control cells, while in patient samples, Y570 phosphorylation was significantly reduced and this activity was correlated with the allelic ratio of the PV mutation in the patient samples (FIG. 18). These results, together with results from FIGS. 13, 14, and 17, show that the level of Ser523 and Tyr 570 phosphorylation can be used as biomarkers for MPN disease and its activity.

The invention claimed is:

1. An assay for screening and identifying a modulator of JH2 kinase activity, comprising:
   a) reacting a test substance with a reaction mixture comprising a JH2 domain, ATP or an analog thereof, divalent cations, and optionally, a substrate for the kinase activity of JH2, and
   b) determining in said reaction mixture of step 1) at least one feature selected from the group consisting of JH2 autophosphorylation, substrate phosphorylation, binding of ATP or an analog thereof to the JH2 domain, binding of the test substance to the JH2 domain, binding of the substrate to the JH2 domain, ADP production, and a conformational or structural state of JH2, and
   c) identifying said test substance as a modulator of JH2 kinase activity if the feature determined in step b) is different from the corresponding feature determined in the absence of said test substance.

2. The assay according to claim 1, wherein said phosphorylation refers to tyrosine phosphorylation.

3. The assay according to claim 2, wherein said tyrosine phosphorylation is determined by an antibody specific for phosphorylated Tyr570 of JAK2.

4. The assay according to claim 1, wherein said reaction mixture comprises a substrate for the tyrosine kinase activity of JH2.

5. The assay according to claim 4, wherein the level of tyrosine phosphorylation in said substrate is determined by a phosphotyrosine specific antibody.

6. The assay according to claim 1, wherein said phosphorylation refers to serine phosphorylation.

7. The assay according to claim 6, wherein said serine residue is Ser523 of JAK2.

8. The assay according to claim 1, wherein said reaction mixture comprises a substrate for the serine kinase activity of JH2.

9. The assay according to claim 8, wherein the level of serine phosphorylation in said substrate is determined by a phosphoserine specific antibody.

10. The assay according to claim 1, wherein the level of phosphorylation is determined by a method selected from the group consisting of mass spectrometry, microscopy, spectroscopy, western blotting, and immunoassays.

11. The assay according to claim 1, wherein the level of binding is determined by a method selected from the group consisting of measuring a calorimetric change in the melting temperature or enthalpy of JH2; measuring surface plasmon resonance changes in JH2, substrate, test substance or ATP or an analog thereof: spectroscopy including fluorescence, UV/visible light, CD, and NMR based methods; and microscopy including atom force microscopy and crystallography.

12. The assay according to claim 1, which is based on competition with the test substance.

13. The assay according to claim 1, wherein said JH2 domain is expressed in a cell line, and the assay comprises an additional step prior to step a) wherein said cells are lysed and, optionally, the JH2 domain is purified.

14. The assay according to claim 13, wherein said cell line is deficient in the JAK kinase in question.

15. The assay according to claim 1, wherein the JH2 domain is selected from the group consisting of JAK1, JAK2, JAK3 and TYK2 JH2 domains.

16. The assay according to claim 1, wherein said JH2 domain comprises an amino acid sequence selected from the group consisting of amino acids 553-856, 567-856 or 574-856 of SEQ ID NO. 1; amino acids 513-827 or 523-827 of SEQ ID NO. 2; amino acids 512-800 or 521-777 of SEQ ID NO. 3; and amino acids 564-876, 577-876, or 571-876 of SEQ ID NO. 4.

17. The assay according to claim 1, wherein the JH2 domain is comprised in a polypeptide further comprising one or more other JAK domains, or is comprised in a full length JAK polypeptide.

18. The assay according to claim 17, wherein said other JAK domain or JAK polypeptide comprises activation loop tyrosines of JH1 selected from the group consisting of amino acids Tyr1007/1008 of SEQ ID NO. 2, Tyr980/981 of SEQ ID NO. 3, Tyr 1034/1035 of SEQ ID NO. 1 and Tyr1054/1055 of SEQ ID NO. 4.

19. The assay according to claim 15, wherein said polypeptide comprises a mutation causing aberrant JAK signaling.

20. The assay according to claim 19, wherein said mutation is a hyperactivating mutation selected from the group consisting of JAK2-V617F, JAK2-M531I, JAK2-F537I, JAK2-K539L, JAK2-F537-K539delinsL, JAK2-H538QK539L, JAK2-H538D+K539L+I546S, JAK2, -H538-K539del, JAK2-D620E, JAK2-V617FD629E, JAK2-V617FC618R, JAK2-V617FC616Y and JAK2-L611S, JAK2-K607N, JAK2-T875N, JAK3-A572V, JAK3-A573V, JAK3-A593T+A573V, JAK3-V722I, JAK3-P132T, JAK1-T478S, JAK1-S512L, JAK1-V623A, JAK1-A634D, JAK1-V658F, JAK1-R724H, and JAK1-L683F.

21. An assay for screening and identifying a modulator of JAK kinase activity, comprising:
   a) expressing a JAK peptide comprising a catalytically active form of a JH2 domain in vivo in a prokaryotic or non-human eukaryotic organism,
   b) administering a test substance to said organism,
   c) determining a physiological readout, and
   d) identifying said test substance as a modulator of JAK kinase activity if the physiological readout in step c) is different from the physiological readout in the absence of said test substance.

22. The assay according to claim 21, wherein said readout is selected from the group consisting of development of an immunological disease, an immune response, a hematopoietic disease or lineage, tumor, a disease of central or peripheral neural system, a metabolic or cardiac disease and a physiological response including growth, development, reproduction and lactation.

* * * * *

```
                         SEQUENCE LISTING

<160> NUMBER OF SEQ ID NOS: 4

<210> SEQ ID NO 1
<211> LENGTH: 1154
<212> TYPE: PRT
<213> ORGANISM: Homo sapiens

<400> SEQUENCE: 1

Met Gln Tyr Leu Asn Ile Lys Glu Asp Cys Asn Ala Met Ala Phe Cys
1               5                   10                  15

Ala Lys Met Arg Ser Ser Lys Lys Thr Glu Val Asn Leu Glu Ala Pro
            20                  25                  30

Glu Pro Gly Val Glu Val Ile Phe Tyr Leu Ser Asp Arg Glu Pro Leu
        35                  40                  45

Arg Leu Gly Ser Gly Glu Tyr Thr Ala Glu Glu Leu Cys Ile Arg Ala
    50                  55                  60

Ala Gln Ala Cys Arg Ile Ser Pro Leu Cys His Asn Leu Phe Ala Leu
65                  70                  75                  80

Tyr Asp Glu Asn Thr Lys Leu Trp Tyr Ala Pro Asn Arg Thr Ile Thr
                85                  90                  95

Val Asp Asp Lys Met Ser Leu Arg Leu His Tyr Arg Met Arg Phe Tyr
            100                 105                 110

Phe Thr Asn Trp His Gly Thr Asn Asp Asn Glu Gln Ser Val Trp Arg
        115                 120                 125

His Ser Pro Lys Lys Gln Lys Asn Gly Tyr Glu Lys Lys Lys Ile Pro
    130                 135                 140

Asp Ala Thr Pro Leu Leu Asp Ala Ser Ser Leu Glu Tyr Leu Phe Ala
145                 150                 155                 160

Gln Gly Gln Tyr Asp Leu Val Lys Cys Leu Ala Pro Ile Arg Asp Pro
                165                 170                 175

Lys Thr Glu Gln Asp Gly His Asp Ile Glu Asn Glu Cys Leu Gly Met
            180                 185                 190

Ala Val Leu Ala Ile Ser His Tyr Ala Met Met Lys Lys Met Gln Leu
        195                 200                 205

Pro Glu Leu Pro Lys Asp Ile Ser Tyr Lys Arg Tyr Ile Pro Glu Thr
    210                 215                 220

Leu Asn Lys Ser Ile Arg Gln Arg Asn Leu Leu Thr Arg Met Arg Ile
225                 230                 235                 240

Asn Asn Val Phe Lys Asp Phe Leu Lys Glu Phe Asn Asn Lys Thr Ile
                245                 250                 255

Cys Asp Ser Ser Val Ser Thr His Asp Leu Lys Val Lys Tyr Leu Ala
            260                 265                 270

Thr Leu Glu Thr Leu Thr Lys His Tyr Gly Ala Glu Ile Phe Glu Thr
        275                 280                 285

Ser Met Leu Leu Ile Ser Ser Glu Asn Glu Met Asn Trp Phe His Ser
    290                 295                 300

Asn Asp Gly Gly Asn Val Leu Tyr Tyr Glu Val Met Val Thr Gly Asn
305                 310                 315                 320

Leu Gly Ile Gln Trp Arg His Lys Pro Asn Val Val Ser Val Glu Lys
                325                 330                 335

Glu Lys Asn Lys Leu Lys Arg Lys Lys Leu Glu Asn Lys His Lys Lys
            340                 345                 350
```

```
Asp Glu Glu Lys Asn Lys Ile Arg Glu Glu Trp Asn Asn Phe Ser Tyr
            355                 360                 365
Phe Pro Glu Ile Thr His Ile Val Ile Lys Glu Ser Val Val Ser Ile
370                 375                 380
Asn Lys Gln Asp Asn Lys Lys Met Glu Leu Lys Leu Ser Ser His Glu
385                 390                 395                 400
Glu Ala Leu Ser Phe Val Ser Leu Val Asp Gly Tyr Phe Arg Leu Thr
                405                 410                 415
Ala Asp Ala His His Tyr Leu Cys Thr Asp Val Ala Pro Pro Leu Ile
            420                 425                 430
Val His Asn Ile Gln Asn Gly Cys His Gly Pro Ile Cys Thr Glu Tyr
        435                 440                 445
Ala Ile Asn Lys Leu Arg Gln Glu Gly Ser Glu Glu Gly Met Tyr Val
    450                 455                 460
Leu Arg Trp Ser Cys Thr Asp Phe Asp Asn Ile Leu Met Thr Val Thr
465                 470                 475                 480
Cys Phe Glu Lys Ser Glu Gln Val Gln Gly Ala Gln Lys Gln Phe Lys
                485                 490                 495
Asn Phe Gln Ile Glu Val Gln Lys Gly Arg Tyr Ser Leu His Gly Ser
            500                 505                 510
Asp Arg Ser Phe Pro Ser Leu Gly Asp Leu Met Ser His Leu Lys Lys
        515                 520                 525
Gln Ile Leu Arg Thr Asp Asn Ile Ser Phe Met Leu Lys Arg Cys Cys
    530                 535                 540
Gln Pro Lys Pro Arg Glu Ile Ser Asn Leu Leu Val Ala Thr Lys Lys
545                 550                 555                 560
Ala Gln Glu Trp Gln Pro Val Tyr Pro Met Ser Gln Leu Ser Phe Asp
                565                 570                 575
Arg Ile Leu Lys Lys Asp Leu Val Gln Gly Glu His Leu Gly Arg Gly
            580                 585                 590
Thr Arg Thr His Ile Tyr Ser Gly Thr Leu Met Asp Tyr Lys Asp Asp
        595                 600                 605
Glu Gly Thr Ser Glu Glu Lys Lys Ile Lys Val Ile Leu Lys Val Leu
    610                 615                 620
Asp Pro Ser His Arg Asp Ile Ser Leu Ala Phe Phe Glu Ala Ala Ser
625                 630                 635                 640
Met Met Arg Gln Val Ser His Lys His Ile Val Tyr Leu Tyr Gly Val
                645                 650                 655
Cys Val Arg Asp Val Glu Asn Ile Met Val Glu Glu Phe Val Glu Gly
            660                 665                 670
Gly Pro Leu Asp Leu Phe Met His Arg Lys Ser Asp Val Leu Thr Thr
        675                 680                 685
Pro Trp Lys Phe Lys Val Ala Lys Gln Leu Ala Ser Ala Leu Ser Tyr
    690                 695                 700
Leu Glu Asp Lys Asp Leu Val His Gly Asn Val Cys Thr Lys Asn Leu
705                 710                 715                 720
Leu Leu Ala Arg Glu Gly Ile Asp Ser Glu Cys Gly Pro Phe Ile Lys
                725                 730                 735
Leu Ser Asp Pro Gly Ile Pro Ile Thr Val Leu Ser Arg Gln Glu Cys
            740                 745                 750
Ile Glu Arg Ile Pro Trp Ile Ala Pro Glu Cys Val Glu Asp Ser Lys
        755                 760                 765
Asn Leu Ser Val Ala Ala Asp Lys Trp Ser Phe Gly Thr Thr Leu Trp
```

```
                770                 775                 780
Glu Ile Cys Tyr Asn Gly Glu Ile Pro Leu Lys Asp Lys Thr Leu Ile
785                 790                 795                 800

Glu Lys Glu Arg Phe Tyr Glu Ser Arg Cys Arg Pro Val Thr Pro Ser
                805                 810                 815

Cys Lys Glu Leu Ala Asp Leu Met Thr Arg Cys Met Asn Tyr Asp Pro
            820                 825                 830

Asn Gln Arg Pro Phe Phe Arg Ala Ile Met Arg Asp Ile Asn Lys Leu
            835                 840                 845

Glu Glu Gln Asn Pro Asp Ile Val Ser Glu Lys Lys Pro Ala Thr Glu
        850                 855                 860

Val Asp Pro Thr His Phe Glu Lys Arg Phe Leu Lys Arg Ile Arg Asp
865                 870                 875                 880

Leu Gly Glu Gly His Phe Gly Lys Val Glu Leu Cys Arg Tyr Asp Pro
                885                 890                 895

Glu Gly Asp Asn Thr Gly Glu Gln Val Ala Val Lys Ser Leu Lys Pro
            900                 905                 910

Glu Ser Gly Gly Asn His Ile Ala Asp Leu Lys Lys Glu Ile Glu Ile
            915                 920                 925

Leu Arg Asn Leu Tyr His Glu Asn Ile Val Lys Tyr Lys Gly Ile Cys
        930                 935                 940

Thr Glu Asp Gly Gly Asn Gly Ile Lys Leu Ile Met Glu Phe Leu Pro
945                 950                 955                 960

Ser Gly Ser Leu Lys Glu Tyr Leu Pro Lys Asn Lys Asn Lys Ile Asn
                965                 970                 975

Leu Lys Gln Gln Leu Lys Tyr Ala Val Gln Ile Cys Lys Gly Met Asp
            980                 985                 990

Tyr Leu Gly Ser Arg Gln Tyr Val His Arg Asp Leu Ala Ala Arg Asn
            995                 1000                1005

Val Leu Val Glu Ser Glu His Gln Val Lys Ile Gly Asp Phe Gly
        1010                1015                1020

Leu Thr Lys Ala Ile Glu Thr Asp Lys Glu Tyr Tyr Thr Val Lys
        1025                1030                1035

Asp Asp Arg Asp Ser Pro Val Phe Trp Tyr Ala Pro Glu Cys Leu
        1040                1045                1050

Met Gln Ser Lys Phe Tyr Ile Ala Ser Asp Val Trp Ser Phe Gly
        1055                1060                1065

Val Thr Leu His Glu Leu Leu Thr Tyr Cys Asp Ser Asp Ser Ser
        1070                1075                1080

Pro Met Ala Leu Phe Leu Lys Met Ile Gly Pro Thr His Gly Gln
        1085                1090                1095

Met Thr Val Thr Arg Leu Val Asn Thr Leu Lys Glu Gly Lys Arg
        1100                1105                1110

Leu Pro Cys Pro Pro Asn Cys Pro Asp Glu Val Tyr Gln Leu Met
        1115                1120                1125

Arg Lys Cys Trp Glu Phe Gln Pro Ser Asn Arg Thr Ser Phe Gln
        1130                1135                1140

Asn Leu Ile Glu Gly Phe Glu Ala Leu Leu Lys
        1145                1150

<210> SEQ ID NO 2
<211> LENGTH: 1132
<212> TYPE: PRT
<213> ORGANISM: Homo sapiens
```

-continued

<400> SEQUENCE: 2

```
Met Gly Met Ala Cys Leu Thr Met Thr Glu Met Glu Gly Thr Ser Thr
1               5                   10                  15

Ser Ser Ile Tyr Gln Asn Gly Asp Ile Ser Gly Asn Ala Asn Ser Met
            20                  25                  30

Lys Gln Ile Asp Pro Val Leu Gln Val Tyr Leu Tyr His Ser Leu Gly
        35                  40                  45

Lys Ser Glu Ala Asp Tyr Leu Thr Phe Pro Ser Gly Glu Tyr Val Ala
50                  55                  60

Glu Glu Ile Cys Ile Ala Ala Ser Lys Ala Cys Gly Ile Thr Pro Val
65                  70                  75                  80

Tyr His Asn Met Phe Ala Leu Met Ser Glu Thr Glu Arg Ile Trp Tyr
                85                  90                  95

Pro Pro Asn His Val Phe His Ile Asp Glu Ser Thr Arg His Asn Val
            100                 105                 110

Leu Tyr Arg Ile Arg Phe Tyr Phe Pro Arg Trp Tyr Cys Ser Gly Ser
        115                 120                 125

Asn Arg Ala Tyr Arg His Gly Ile Ser Arg Gly Ala Glu Ala Pro Leu
    130                 135                 140

Leu Asp Asp Phe Val Met Ser Tyr Leu Phe Ala Gln Trp Arg His Asp
145                 150                 155                 160

Phe Val His Gly Trp Ile Lys Val Pro Val Thr His Glu Thr Gln Glu
                165                 170                 175

Glu Cys Leu Gly Met Ala Val Leu Asp Met Met Arg Ile Ala Lys Glu
            180                 185                 190

Asn Asp Gln Thr Pro Leu Ala Ile Tyr Asn Ser Ile Ser Tyr Lys Thr
        195                 200                 205

Phe Leu Pro Lys Cys Ile Arg Ala Lys Ile Gln Asp Tyr His Ile Leu
    210                 215                 220

Thr Arg Lys Arg Ile Arg Tyr Arg Phe Arg Arg Phe Ile Gln Gln Phe
225                 230                 235                 240

Ser Gln Cys Lys Ala Thr Ala Arg Asn Leu Lys Leu Lys Tyr Leu Ile
                245                 250                 255

Asn Leu Glu Thr Leu Gln Ser Ala Phe Tyr Thr Glu Lys Phe Glu Val
            260                 265                 270

Lys Glu Pro Gly Ser Gly Pro Ser Gly Glu Glu Ile Phe Ala Thr Ile
        275                 280                 285

Ile Ile Thr Gly Asn Gly Gly Ile Gln Trp Ser Arg Gly Lys His Lys
    290                 295                 300

Glu Ser Glu Thr Leu Thr Glu Gln Asp Leu Gln Leu Tyr Cys Asp Phe
305                 310                 315                 320

Pro Asn Ile Ile Asp Val Ser Ile Lys Gln Ala Asn Gln Glu Gly Ser
                325                 330                 335

Asn Glu Ser Arg Val Val Thr Ile His Lys Gln Asp Gly Lys Asn Leu
            340                 345                 350

Glu Ile Glu Leu Ser Ser Leu Arg Glu Ala Leu Ser Phe Val Ser Leu
        355                 360                 365

Ile Asp Gly Tyr Tyr Arg Leu Thr Ala Asp Ala His His Tyr Leu Cys
    370                 375                 380

Lys Glu Val Ala Pro Pro Ala Val Leu Glu Asn Ile Gln Ser Asn Cys
385                 390                 395                 400

His Gly Pro Ile Ser Met Asp Phe Ala Ile Ser Lys Leu Lys Lys Ala
```

-continued

```
                405                 410                 415
Gly Asn Gln Thr Gly Leu Tyr Val Leu Arg Cys Ser Pro Lys Asp Phe
            420                 425                 430

Asn Lys Tyr Phe Leu Thr Phe Ala Val Glu Arg Glu Asn Val Ile Glu
            435                 440                 445

Tyr Lys His Cys Leu Ile Thr Lys Asn Glu Asn Glu Glu Tyr Asn Leu
            450                 455                 460

Ser Gly Thr Lys Lys Asn Phe Ser Ser Leu Lys Asp Leu Leu Asn Cys
465                 470                 475                 480

Tyr Gln Met Glu Thr Val Arg Ser Asp Asn Ile Ile Phe Gln Phe Thr
            485                 490                 495

Lys Cys Cys Pro Pro Lys Pro Lys Asp Lys Ser Asn Leu Leu Val Phe
            500                 505                 510

Arg Thr Asn Gly Val Ser Asp Val Pro Thr Ser Pro Thr Leu Gln Arg
            515                 520                 525

Pro Thr His Met Asn Gln Met Val Phe His Lys Ile Arg Asn Glu Asp
            530                 535                 540

Leu Ile Phe Asn Glu Ser Leu Gly Gln Gly Thr Phe Thr Lys Ile Phe
545                 550                 555                 560

Lys Gly Val Arg Arg Glu Val Gly Asp Tyr Gly Gln Leu His Glu Thr
                565                 570                 575

Glu Val Leu Leu Lys Val Leu Asp Lys Ala His Arg Asn Tyr Ser Glu
                580                 585                 590

Ser Phe Phe Glu Ala Ala Ser Met Met Ser Lys Leu Ser His Lys His
                595                 600                 605

Leu Val Leu Asn Tyr Gly Val Cys Val Cys Gly Asp Glu Asn Ile Leu
            610                 615                 620

Val Gln Glu Phe Val Lys Phe Gly Ser Leu Asp Thr Tyr Leu Lys Lys
625                 630                 635                 640

Asn Lys Asn Cys Ile Asn Ile Leu Trp Lys Leu Glu Val Ala Lys Gln
                645                 650                 655

Leu Ala Trp Ala Met His Phe Leu Glu Glu Asn Thr Leu Ile His Gly
            660                 665                 670

Asn Val Cys Ala Lys Asn Ile Leu Leu Ile Arg Glu Glu Asp Arg Lys
            675                 680                 685

Thr Gly Asn Pro Pro Phe Ile Lys Leu Ser Asp Pro Gly Ile Ser Ile
            690                 695                 700

Thr Val Leu Pro Lys Asp Ile Leu Gln Glu Arg Ile Pro Trp Val Pro
705                 710                 715                 720

Pro Glu Cys Ile Glu Asn Pro Lys Asn Leu Asn Leu Ala Thr Asp Lys
                725                 730                 735

Trp Ser Phe Gly Thr Thr Leu Trp Glu Ile Cys Ser Gly Gly Asp Lys
            740                 745                 750

Pro Leu Ser Ala Leu Asp Ser Gln Arg Lys Leu Gln Phe Tyr Glu Asp
            755                 760                 765

Arg His Gln Leu Pro Ala Pro Lys Trp Ala Glu Leu Ala Asn Leu Ile
            770                 775                 780

Asn Asn Cys Met Asp Tyr Glu Pro Asp Phe Arg Pro Ser Phe Arg Ala
785                 790                 795                 800

Ile Ile Arg Asp Leu Asn Ser Leu Phe Thr Pro Asp Tyr Glu Leu Leu
                805                 810                 815

Thr Glu Asn Asp Met Leu Pro Asn Met Arg Ile Gly Ala Leu Gly Phe
                820                 825                 830
```

```
Ser Gly Ala Phe Glu Asp Arg Asp Pro Thr Gln Phe Glu Glu Arg His
        835                 840                 845

Leu Lys Phe Leu Gln Gln Leu Gly Lys Gly Asn Phe Gly Ser Val Glu
        850                 855                 860

Met Cys Arg Tyr Asp Pro Leu Gln Asp Asn Thr Gly Glu Val Val Ala
865                 870                 875                 880

Val Lys Lys Leu Gln His Ser Thr Glu Glu His Leu Arg Asp Phe Glu
                885                 890                 895

Arg Glu Ile Glu Ile Leu Lys Ser Leu Gln His Asp Asn Ile Val Lys
            900                 905                 910

Tyr Lys Gly Val Cys Tyr Ser Ala Gly Arg Arg Asn Leu Lys Leu Ile
        915                 920                 925

Met Glu Tyr Leu Pro Tyr Gly Ser Leu Arg Asp Tyr Leu Gln Lys His
    930                 935                 940

Lys Glu Arg Ile Asp His Ile Lys Leu Leu Gln Tyr Thr Ser Gln Ile
945                 950                 955                 960

Cys Lys Gly Met Glu Tyr Leu Gly Thr Lys Arg Tyr Ile His Arg Asp
                965                 970                 975

Leu Ala Thr Arg Asn Ile Leu Val Glu Asn Glu Asn Arg Val Lys Ile
            980                 985                 990

Gly Asp Phe Gly Leu Thr Lys Val Leu Pro Gln Asp Lys Glu Tyr Tyr
        995                 1000                1005

Lys Val Lys Glu Pro Gly Glu Ser Pro Ile Phe Trp Tyr Ala Pro
    1010                1015                1020

Glu Ser Leu Thr Glu Ser Lys Phe Ser Val Ala Ser Asp Val Trp
    1025                1030                1035

Ser Phe Gly Val Val Leu Tyr Glu Leu Phe Thr Tyr Ile Glu Lys
    1040                1045                1050

Ser Lys Ser Pro Pro Ala Glu Phe Met Arg Met Ile Gly Asn Asp
    1055                1060                1065

Lys Gln Gly Gln Met Ile Val Phe His Leu Ile Glu Leu Leu Lys
    1070                1075                1080

Asn Asn Gly Arg Leu Pro Arg Pro Asp Gly Cys Pro Asp Glu Ile
    1085                1090                1095

Tyr Met Ile Met Thr Glu Cys Trp Asn Asn Asn Val Asn Gln Arg
    1100                1105                1110

Pro Ser Phe Arg Asp Leu Ala Leu Arg Val Asp Gln Ile Arg Asp
    1115                1120                1125

Asn Met Ala Gly
    1130

<210> SEQ ID NO 3
<211> LENGTH: 1131
<212> TYPE: PRT
<213> ORGANISM: Homo sapiens

<400> SEQUENCE: 3

Met Ala Pro Pro Ser Glu Glu Thr Pro Leu Ile Pro Gln Arg Ser Cys
1               5                   10                  15

Ser Leu Leu Ser Thr Glu Ala Gly Ala Leu His Val Leu Leu Pro Ala
                20                  25                  30

Arg Gly Pro Gly Pro Pro Gln Arg Leu Ser Phe Ser Phe Gly Asp His
            35                  40                  45

Leu Ala Glu Asp Leu Cys Val Gln Ala Ala Lys Ala Ser Gly Ile Leu
```

-continued

```
               50                  55                  60
Pro Val Tyr His Ser Leu Phe Ala Leu Ala Thr Glu Asp Leu Ser Cys
65                   70                  75                  80

Trp Phe Pro Pro Ser His Ile Phe Ser Val Glu Asp Ala Ser Thr Gln
                85                  90                  95

Val Leu Leu Tyr Arg Ile Arg Phe Tyr Phe Pro Asn Trp Phe Gly Leu
                100                 105                 110

Glu Lys Cys His Arg Phe Gly Leu Arg Lys Asp Leu Ala Ser Ala Ile
            115                 120                 125

Leu Asp Leu Pro Val Leu Glu His Leu Phe Ala Gln His Arg Ser Asp
130                 135                 140

Leu Val Ser Gly Arg Leu Pro Val Gly Leu Ser Leu Lys Glu Gln Gly
145                 150                 155                 160

Glu Cys Leu Ser Leu Ala Val Leu Asp Leu Ala Arg Met Ala Arg Glu
                165                 170                 175

Gln Ala Gln Arg Pro Gly Glu Leu Leu Lys Thr Val Ser Tyr Lys Ala
                180                 185                 190

Cys Leu Pro Pro Ser Leu Arg Asp Leu Ile Gln Gly Leu Ser Phe Val
            195                 200                 205

Thr Arg Arg Arg Ile Arg Arg Thr Val Arg Arg Ala Leu Arg Arg Val
210                 215                 220

Ala Ala Cys Gln Ala Asp Arg His Ser Leu Met Ala Lys Tyr Ile Met
225                 230                 235                 240

Asp Leu Glu Arg Leu Asp Pro Ala Gly Ala Ala Glu Thr Phe His Val
                245                 250                 255

Gly Leu Pro Gly Ala Leu Gly Gly His Asp Gly Leu Gly Leu Leu Arg
                260                 265                 270

Val Ala Gly Asp Gly Gly Ile Ala Trp Thr Gln Gly Glu Gln Glu Val
            275                 280                 285

Leu Gln Pro Phe Cys Asp Phe Pro Glu Ile Val Asp Ile Ser Ile Lys
290                 295                 300

Gln Ala Pro Arg Val Gly Pro Ala Gly Glu His Arg Leu Val Thr Val
305                 310                 315                 320

Thr Arg Thr Asp Asn Gln Ile Leu Glu Ala Glu Phe Pro Gly Leu Pro
                325                 330                 335

Glu Ala Leu Ser Phe Val Ala Leu Val Asp Gly Tyr Phe Arg Leu Thr
                340                 345                 350

Thr Asp Ser Gln His Phe Phe Cys Lys Glu Val Ala Pro Pro Arg Leu
            355                 360                 365

Leu Glu Glu Val Ala Glu Gln Cys His Gly Pro Ile Thr Leu Asp Phe
370                 375                 380

Ala Ile Asn Lys Leu Lys Thr Gly Gly Ser Arg Pro Gly Ser Tyr Val
385                 390                 395                 400

Leu Arg Arg Ser Pro Gln Asp Phe Asp Ser Phe Leu Leu Thr Val Cys
                405                 410                 415

Val Gln Asn Pro Leu Gly Pro Asp Tyr Lys Gly Cys Leu Ile Arg Arg
                420                 425                 430

Ser Pro Thr Gly Thr Phe Leu Leu Val Gly Leu Ser Arg Pro His Ser
            435                 440                 445

Ser Leu Arg Glu Leu Leu Ala Thr Cys Trp Asp Gly Gly Leu His Val
450                 455                 460

Asp Gly Val Ala Val Thr Leu Thr Ser Cys Cys Ile Pro Arg Pro Lys
465                 470                 475                 480
```

-continued

```
Glu Lys Ser Asn Leu Ile Val Val Gln Arg Gly His Ser Pro Pro Thr
                485                 490                 495
Ser Ser Leu Val Gln Pro Gln Ser Gln Tyr Gln Leu Ser Gln Met Thr
            500                 505                 510
Phe His Lys Ile Pro Ala Asp Ser Leu Glu Trp His Glu Asn Leu Gly
        515                 520                 525
His Gly Ser Phe Thr Lys Ile Tyr Arg Gly Cys Arg His Glu Val Val
    530                 535                 540
Asp Gly Glu Ala Arg Lys Thr Glu Val Leu Leu Lys Val Met Asp Ala
545                 550                 555                 560
Lys His Lys Asn Cys Met Glu Ser Phe Leu Glu Ala Ala Ser Leu Met
                565                 570                 575
Ser Gln Val Ser Tyr Arg His Leu Val Leu Leu His Gly Val Cys Met
            580                 585                 590
Ala Gly Asp Ser Thr Met Val Gln Glu Phe Val His Leu Gly Ala Ile
        595                 600                 605
Asp Met Tyr Leu Arg Lys Arg Gly His Leu Val Pro Ala Ser Trp Lys
    610                 615                 620
Leu Gln Val Val Lys Gln Leu Ala Tyr Ala Leu Asn Tyr Leu Glu Asp
625                 630                 635                 640
Lys Gly Leu Pro His Gly Asn Val Ser Ala Arg Lys Val Leu Leu Ala
                645                 650                 655
Arg Glu Gly Ala Asp Gly Ser Pro Pro Phe Ile Lys Leu Ser Asp Pro
            660                 665                 670
Gly Val Ser Pro Ala Val Leu Ser Leu Glu Met Leu Thr Asp Arg Ile
        675                 680                 685
Pro Trp Val Ala Pro Glu Cys Leu Arg Glu Ala Gln Thr Leu Ser Leu
    690                 695                 700
Glu Ala Asp Lys Trp Gly Phe Gly Ala Thr Val Trp Glu Val Phe Ser
705                 710                 715                 720
Gly Val Thr Met Pro Ile Ser Ala Leu Asp Pro Ala Lys Lys Leu Gln
                725                 730                 735
Phe Tyr Glu Asp Arg Gln Gln Leu Pro Ala Pro Lys Trp Thr Glu Leu
            740                 745                 750
Ala Leu Leu Ile Gln Gln Cys Met Ala Tyr Glu Pro Val Gln Arg Pro
        755                 760                 765
Ser Phe Arg Ala Val Ile Arg Asp Leu Asn Ser Leu Ile Ser Ser Asp
    770                 775                 780
Tyr Glu Leu Leu Ser Asp Pro Thr Pro Gly Ala Leu Ala Pro Arg Asp
785                 790                 795                 800
Gly Leu Trp Asn Gly Ala Gln Leu Tyr Ala Cys Gln Asp Pro Thr Ile
                805                 810                 815
Phe Glu Glu Arg His Leu Lys Tyr Ile Ser Gln Leu Gly Lys Gly Asn
            820                 825                 830
Phe Gly Ser Val Glu Leu Cys Arg Tyr Asp Pro Leu Gly Asp Asn Thr
        835                 840                 845
Gly Ala Leu Val Ala Val Lys Gln Leu Gln His Ser Gly Pro Asp Gln
    850                 855                 860
Gln Arg Asp Phe Gln Arg Glu Ile Gln Ile Leu Lys Ala Leu His Ser
865                 870                 875                 880
Asp Phe Ile Val Lys Tyr Arg Gly Val Ser Tyr Gly Pro Gly Arg Gln
                885                 890                 895
```

```
Ser Leu Arg Leu Val Met Glu Tyr Leu Pro Ser Gly Cys Leu Arg Asp
            900                 905                 910

Phe Leu Gln Arg His Arg Ala Arg Leu Asp Ala Ser Arg Leu Leu Leu
            915                 920                 925

Tyr Ser Ser Gln Ile Cys Lys Gly Met Glu Tyr Leu Gly Ser Arg Arg
            930                 935                 940

Cys Val His Arg Asp Leu Ala Ala Arg Asn Ile Leu Val Glu Ser Glu
945                 950                 955                 960

Ala His Val Lys Ile Ala Asp Phe Gly Leu Ala Lys Leu Leu Pro Leu
                965                 970                 975

Asp Lys Asp Tyr Tyr Val Val Arg Glu Pro Gly Gln Ser Pro Ile Phe
            980                 985                 990

Trp Tyr Ala Pro Glu Ser Leu Ser Asp Asn Ile Phe Ser Arg Gln Ser
            995                 1000                1005

Asp Val Trp Ser Phe Gly Val Val Leu Tyr Glu Leu Phe Thr Tyr
        1010                1015                1020

Cys Asp Lys Ser Cys Ser Pro Ser Ala Glu Phe Leu Arg Met Met
        1025                1030                1035

Gly Cys Glu Arg Asp Val Pro Ala Leu Cys Arg Leu Leu Glu Leu
        1040                1045                1050

Leu Glu Glu Gly Gln Arg Leu Pro Ala Pro Pro Ala Cys Pro Ala
        1055                1060                1065

Glu Val Ser Cys Tyr Ser Gly Trp Arg Asp Ile Cys Ser Met
        1070                1075                1080

Gly Trp Trp Pro Thr Val Ile Ser Arg Trp Asp Leu Ala Cys Ser
        1085                1090                1095

Pro Cys Pro Arg Pro Leu Thr Ile Thr Ala Thr Val Gln Leu
        1100                1105                1110

Pro Pro Thr Leu His Ala Thr Ala Ala Ser Val Ala Val Pro Asn
        1115                1120                1125

Lys Thr Cys
        1130

<210> SEQ ID NO 4
<211> LENGTH: 1187
<212> TYPE: PRT
<213> ORGANISM: Homo sapiens

<400> SEQUENCE: 4

Met Pro Leu Arg His Trp Gly Met Ala Arg Gly Ser Lys Pro Val Gly
1               5                   10                  15

Asp Gly Ala Gln Pro Met Ala Ala Met Gly Gly Leu Lys Val Leu Leu
            20                  25                  30

His Trp Ala Gly Pro Gly Gly Gly Glu Pro Trp Val Thr Phe Ser Glu
        35                  40                  45

Ser Ser Leu Thr Ala Glu Glu Val Cys Ile His Ile Ala His Lys Val
    50                  55                  60

Gly Ile Thr Pro Pro Cys Phe Asn Leu Phe Ala Leu Phe Asp Ala Gln
65                  70                  75                  80

Ala Gln Val Trp Leu Pro Pro Asn His Ile Leu Glu Ile Pro Arg Asp
                85                  90                  95

Ala Ser Leu Met Leu Tyr Phe Arg Ile Arg Phe Tyr Phe Arg Asn Trp
            100                 105                 110

His Gly Met Asn Pro Arg Glu Pro Ala Val Tyr Arg Cys Gly Pro Pro
        115                 120                 125
```

-continued

Gly Thr Glu Ala Ser Ser Asp Gln Thr Ala Gln Gly Met Gln Leu Leu
130                 135                 140

Asp Pro Ala Ser Phe Glu Tyr Leu Phe Glu Gln Gly Lys His Glu Phe
145                 150                 155                 160

Val Asn Asp Val Ala Ser Leu Trp Glu Leu Ser Thr Glu Glu Glu Ile
            165                 170                 175

His His Phe Lys Asn Glu Ser Leu Gly Met Ala Phe Leu His Leu Cys
        180                 185                 190

His Leu Ala Leu Arg His Gly Ile Pro Leu Glu Glu Val Ala Lys Lys
    195                 200                 205

Thr Ser Phe Lys Asp Cys Ile Pro Arg Ser Phe Arg Arg His Ile Arg
210                 215                 220

Gln His Ser Ala Leu Thr Arg Leu Arg Leu Arg Asn Val Phe Arg Arg
225                 230                 235                 240

Phe Leu Arg Asp Phe Gln Pro Gly Arg Leu Ser Gln Gln Met Val Met
                245                 250                 255

Val Lys Tyr Leu Ala Thr Leu Glu Arg Leu Ala Pro Arg Phe Gly Thr
            260                 265                 270

Glu Arg Val Pro Val Cys His Leu Arg Leu Leu Ala Gln Ala Glu Gly
        275                 280                 285

Glu Pro Cys Tyr Ile Arg Asp Ser Gly Val Ala Pro Thr Asp Pro Gly
290                 295                 300

Pro Glu Ser Ala Ala Gly Pro Pro Thr His Glu Val Leu Val Thr Gly
305                 310                 315                 320

Thr Gly Gly Ile Gln Trp Trp Pro Val Glu Glu Val Asn Lys Glu
                325                 330                 335

Glu Gly Ser Ser Gly Ser Ser Gly Arg Asn Pro Gln Ala Ser Leu Phe
            340                 345                 350

Gly Lys Lys Ala Lys Ala His Lys Ala Val Gly Gln Pro Ala Asp Arg
        355                 360                 365

Pro Arg Glu Pro Leu Trp Ala Tyr Phe Cys Asp Phe Arg Asp Ile Thr
370                 375                 380

His Val Val Leu Lys Glu His Cys Val Ser Ile His Arg Gln Asp Asn
385                 390                 395                 400

Lys Cys Leu Glu Leu Ser Leu Pro Ser Arg Ala Ala Ala Leu Ser Phe
                405                 410                 415

Val Ser Leu Val Asp Gly Tyr Phe Arg Leu Thr Ala Asp Ser Ser His
            420                 425                 430

Tyr Leu Cys His Glu Val Ala Pro Arg Leu Val Met Ser Ile Arg
        435                 440                 445

Asp Gly Ile His Gly Pro Leu Leu Glu Pro Phe Val Gln Ala Lys Leu
450                 455                 460

Arg Pro Glu Asp Gly Leu Tyr Leu Ile His Trp Ser Thr Ser His Pro
465                 470                 475                 480

Tyr Arg Leu Ile Leu Thr Val Ala Gln Arg Ser Gln Ala Pro Asp Gly
                485                 490                 495

Met Gln Ser Leu Arg Leu Arg Lys Phe Pro Ile Glu Gln Gln Asp Gly
            500                 505                 510

Ala Phe Val Leu Glu Gly Trp Gly Arg Ser Phe Pro Ser Val Arg Glu
        515                 520                 525

Leu Gly Ala Ala Leu Gln Gly Cys Leu Leu Arg Ala Gly Asp Asp Cys
530                 535                 540

```
Phe Ser Leu Arg Arg Cys Cys Leu Pro Gln Pro Gly Glu Thr Ser Asn
545                 550                 555                 560

Leu Ile Ile Met Arg Gly Ala Arg Ala Ser Pro Arg Thr Leu Asn Leu
                565                 570                 575

Ser Gln Leu Ser Phe His Arg Val Asp Gln Lys Glu Ile Thr Gln Leu
            580                 585                 590

Ser His Leu Gly Gln Gly Thr Arg Thr Asn Val Tyr Glu Gly Arg Leu
        595                 600                 605

Arg Val Glu Gly Ser Gly Asp Pro Glu Glu Gly Lys Met Asp Asp Glu
    610                 615                 620

Asp Pro Leu Val Pro Gly Arg Asp Arg Gly Gln Glu Leu Arg Val Val
625                 630                 635                 640

Leu Lys Val Leu Asp Pro Ser His His Asp Ile Ala Leu Ala Phe Tyr
                645                 650                 655

Glu Thr Ala Ser Leu Met Ser Gln Val Ser His Thr His Leu Ala Phe
                660                 665                 670

Val His Gly Val Cys Val Arg Gly Pro Glu Asn Ile Met Val Thr Glu
            675                 680                 685

Tyr Val Glu His Gly Pro Leu Asp Val Trp Leu Arg Arg Glu Arg Gly
        690                 695                 700

His Val Pro Met Ala Trp Lys Met Val Val Ala Gln Gln Leu Ala Ser
705                 710                 715                 720

Ala Leu Ser Tyr Leu Glu Asn Lys Asn Leu Val His Gly Asn Val Cys
                725                 730                 735

Gly Arg Asn Ile Leu Leu Ala Arg Leu Gly Leu Ala Glu Gly Thr Ser
                740                 745                 750

Pro Phe Ile Lys Leu Ser Asp Pro Gly Val Gly Leu Gly Ala Leu Ser
            755                 760                 765

Arg Glu Glu Arg Val Glu Arg Ile Pro Trp Leu Ala Pro Glu Cys Leu
        770                 775                 780

Pro Gly Gly Ala Asn Ser Leu Ser Thr Ala Met Asp Lys Trp Gly Phe
785                 790                 795                 800

Gly Ala Thr Leu Leu Glu Ile Cys Phe Asp Gly Glu Ala Pro Leu Gln
                805                 810                 815

Ser Arg Ser Pro Ser Glu Lys Glu His Phe Tyr Gln Arg Gln His Arg
            820                 825                 830

Leu Pro Glu Pro Ser Cys Pro Gln Leu Ala Thr Leu Thr Ser Gln Cys
        835                 840                 845

Leu Thr Tyr Glu Pro Thr Gln Arg Pro Ser Phe Arg Thr Ile Leu Arg
850                 855                 860

Asp Leu Thr Arg Leu Gln Pro His Asn Leu Ala Asp Val Leu Thr Val
865                 870                 875                 880

Asn Pro Asp Ser Pro Ala Ser Asp Pro Thr Val Phe His Lys Arg Tyr
                885                 890                 895

Leu Lys Lys Ile Arg Asp Leu Gly Glu Gly His Phe Gly Lys Val Ser
            900                 905                 910

Leu Tyr Cys Tyr Asp Pro Thr Asn Asp Gly Thr Gly Glu Met Val Ala
        915                 920                 925

Val Lys Ala Leu Lys Ala Asp Cys Gly Pro Gln His Arg Ser Gly Trp
    930                 935                 940

Lys Gln Glu Ile Asp Ile Leu Arg Thr Leu Tyr His Glu His Ile Ile
945                 950                 955                 960

Lys Tyr Lys Gly Cys Cys Glu Asp Gln Gly Glu Lys Ser Leu Gln Leu
```

```
                965                 970                 975
Val Met Glu Tyr Val Pro Leu Gly Ser Leu Arg Asp Tyr Leu Pro Arg
                    980                 985                 990

His Ser Ile Gly Leu Ala Gln Leu Leu Leu Phe Ala Gln Gln Ile Cys
        995                 1000                1005

Glu Gly Met Ala Tyr Leu His Ala Gln His Tyr Ile His Arg Asp
    1010                1015                1020

Leu Ala Ala Arg Asn Val Leu Leu Asp Asn Asp Arg Leu Val Lys
    1025                1030                1035

Ile Gly Asp Phe Gly Leu Ala Lys Ala Val Pro Glu Gly His Glu
    1040                1045                1050

Tyr Tyr Arg Val Arg Glu Asp Gly Asp Ser Pro Val Phe Trp Tyr
    1055                1060                1065

Ala Pro Glu Cys Leu Lys Glu Tyr Lys Phe Tyr Tyr Ala Ser Asp
    1070                1075                1080

Val Trp Ser Phe Gly Val Thr Leu Tyr Glu Leu Leu Thr His Cys
    1085                1090                1095

Asp Ser Ser Gln Ser Pro Pro Thr Lys Phe Leu Glu Leu Ile Gly
    1100                1105                1110

Ile Ala Gln Gly Gln Met Thr Val Leu Arg Leu Thr Glu Leu Leu
    1115                1120                1125

Glu Arg Gly Glu Arg Leu Pro Arg Pro Asp Lys Cys Pro Cys Glu
    1130                1135                1140

Val Tyr His Leu Met Lys Asn Cys Trp Glu Thr Glu Ala Ser Phe
    1145                1150                1155

Arg Pro Thr Phe Glu Asn Leu Ile Pro Ile Leu Lys Thr Val His
    1160                1165                1170

Glu Lys Tyr Gln Gly Gln Ala Pro Ser Val Phe Ser Val Cys
    1175                1180                1185
```